US008779924B2

(12) United States Patent
Pesot et al.

(10) Patent No.: US 8,779,924 B2
(45) Date of Patent: Jul. 15, 2014

(54) NURSE CALL SYSTEM WITH ADDITIONAL STATUS BOARD

(75) Inventors: Whitney W. Pesot, Cary, NC (US); Katherine J. Vigneron, Blaine, MN (US); Michelle E. McCleerey, Raleigh, NC (US); Christian Saucier, Raleigh, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 355 days.

(21) Appl. No.: 12/711,850

(22) Filed: Feb. 24, 2010

(65) Prior Publication Data
US 2011/0205062 A1 Aug. 25, 2011

Related U.S. Application Data

(63) Continuation-in-part of application No. 12/708,950, filed on Feb. 19, 2010, now abandoned.

(51) Int. Cl.
*G08B 23/00* (2006.01)
(52) U.S. Cl.
USPC .......................................... 340/573.1; 705/2
(58) Field of Classification Search
CPC ......... G06F 1/00; G06F 19/10; G06F 19/327; G06Q 50/24; G06Q 50/22; G06Q 25/00; A61B 5/7435; G08B 1/00
USPC ............ 340/573.1, 500, 506, 286.01, 286.06, 340/286.07, 540; 705/2, 3
See application file for complete search history.

(56) References Cited

U.S. PATENT DOCUMENTS

| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |

(Continued)

FOREIGN PATENT DOCUMENTS

| WO | WO 02/091297 | 11/2002 |
| WO | WO 2004/036390 | 4/2004 |

OTHER PUBLICATIONS

"The COMposer™ System, Installation Manual", by Hill-Rom Services Inc., (2003).

(Continued)

*Primary Examiner* — George Bugg
*Assistant Examiner* — Edny Labbees
(74) *Attorney, Agent, or Firm* — Barnes & Thornburg LLP

(57) ABSTRACT

A healthcare information system for use in a healthcare facility having patient beds in a plurality of patient rooms is provided. The healthcare information system has a nurse call computer which is located at a nurse's station and which is configured to receive nurse calls and/or safety alerts originating from the patient rooms. The healthcare information system has a status board computer which is also located at the nurse's station and which is operable to display, for more than one patient, information regarding the patient, staff location, bed data, and room status.

19 Claims, 11 Drawing Sheets

(56) References Cited

U.S. PATENT DOCUMENTS

| | | |
|---|---|---|
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Chahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,262,944 A | 11/1993 | Weisner et al. |
| 5,266,944 A | 11/1993 | Carroll et al. |
| 5,291,399 A | 3/1994 | Chaco |
| 5,319,355 A | 6/1994 | Russek |
| 5,319,363 A | 6/1994 | Welch et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,346 A | 1/2000 | Malone |
| 6,014,633 A | 1/2000 | DeBusk et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |

(56) References Cited

U.S. PATENT DOCUMENTS

| | | | |
|---|---|---|---|
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 6,982,639 B2 * | 1/2006 | Brackett et al. ......... 340/539.13 |
| 7,038,588 B2 | 5/2006 | Boone et al. |
| 7,068,143 B2 | 6/2006 | Doering et al. |
| 7,079,036 B2 | 7/2006 | Cooper et al. |
| 7,092,376 B2 | 8/2006 | Schuman |
| 7,138,902 B2 | 11/2006 | Menard |
| 7,242,306 B2 * | 7/2007 | Wildman et al. ......... 340/573.1 |
| 7,292,135 B2 | 11/2007 | Bixler et al. |
| 7,319,386 B2 * | 1/2008 | Collins et al. ............ 340/539.12 |
| 7,333,002 B2 | 2/2008 | Bixler et al. |
| 7,336,187 B2 | 2/2008 | Hubbard, Jr. et al. |
| 7,526,529 B2 | 4/2009 | Unluturk et al. |
| 7,590,551 B2 | 9/2009 | Auer |
| 7,598,852 B2 | 10/2009 | Chriss |
| 7,612,679 B1 | 11/2009 | Fackler et al. |
| 8,086,728 B2 * | 12/2011 | Nasnas ........................ 709/224 |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0206116 A1 | 11/2003 | Weiner et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2005/0035862 A1 | 2/2005 | Wildman et al. |

(56) References Cited

U.S. PATENT DOCUMENTS

| | | |
|---|---|---|
| 2005/0242946 A1 | 11/2005 | Hubbard, Jr. et al. |
| 2006/0049936 A1 | 3/2006 | Collins, Jr. et al. |
| 2006/0248221 A1 | 11/2006 | Hottel et al. |
| 2008/0018436 A1* | 1/2008 | Traughber et al. ....... 340/286.07 |
| 2008/0021731 A1 | 1/2008 | Rodgers |
| 2009/0212956 A1 | 8/2009 | Schuman et al. |
| 2009/0217080 A1 | 8/2009 | Ferguson et al. |
| 2010/0079276 A1 | 4/2010 | Collins, Jr. et al. |

OTHER PUBLICATIONS

"COMLinx™ Enterprise Solutions, Nurse Communication Module, User's Guide", by Hill-Rom Services, Inc., (2000).

* cited by examiner

NURSE CALL SYSTEM WITH ADDITIONAL STATUS BOARD

CROSS REFERENCE TO RELATED APPLICATIONS

This application is a continuation-in-part of U.S. application Ser. No. 12/708,950, filed Feb. 19, 2010, which is hereby expressly incorporated by reference herein.

BACKGROUND

The present disclosure relates to healthcare information systems such as nurse call systems and bed status systems found in healthcare facilities. More particularly, the present disclosure relates to the handling and display of data associated with patients and the hospital beds on which patients are located, as well as any nurse calls or other types of alert or alarm calls originating from patient rooms.

Nurse call systems used in healthcare facilities, such as hospitals, are known. Patients place nurse calls by pressing a nurse call button on a siderail of a hospital bed or by pressing a nurse call button on a handheld unit known in the art as a pillow speaker. Wall mounted cords or switches may also be used to place nurse calls. Typically, after the nurse call is placed, a nurse at a master station will speak with the patient via an intercom type system to find out why the patient placed the nurse call.

Some nurse call systems are configured to receive and display bed status data to indicate the positions and/or status of various subsystems or portions of the hospital beds that are located in various patient rooms. The bed status data may include, for example, data indicating whether each of the siderails of the bed are up or down, data indicating whether the casters of the bed are braked or unbraked, and data indicating whether an upper frame of the bed is in its lowest position relative to a base frame of the bed. Examples of such prior art nurse call systems are Hill-Rom's COMposer™ communication system and Hill-Rom's COMLinx™ communication system.

Hospitals are continually trying to improve the efficiency of caregivers. In this regard, providing needed information quickly to caregivers without the caregivers having to spend valuable time retrieving the information enhances caregiver efficiency. However, if too much information is provided to caregivers, they can become overwhelmed with the data which results in diminishing, rather than enhancing, caregiver productivity. Striking the right balance between providing too little information to caregivers and too much information to caregivers is no easy task. In the prior art nurse call systems, certain information was available to caregivers only after certain selections on a computer screen were made or certain keyboard entries were made. Such extra steps to retrieve desired information detract from caregiver productivity.

SUMMARY

The present invention comprises one or more of the features recited in the appended claims and/or the following features which, alone or in any combination, may comprise patentable subject matter:

A healthcare information system for use in a healthcare facility having patient beds in a plurality of patient rooms may be provided. The healthcare information system may have a nurse call computer located at a nurse's station. The nurse call computer may include a first display screen. The nurse call computer may be configured to receive nurse calls originating from the patient rooms and to display information about the nurse calls on the first display screen.

The nurse call system may also have a plurality of interface units located in patient rooms. Each interface unit may be configured to receive bed data that pertains to an associated patient bed. Each interface unit may be communicatively coupled to the nurse call computer. The interface units may be spaced from the respective hospital beds or attached to the respective hospital beds or included as part of the respective patient beds. The interface units in some embodiments may be communication circuitry that is included as part of the overall circuitry of the respective hospital beds.

The nurse call system may further have a status board computer also located at the nurse's station. The status board computer may be communicatively coupled to the plurality of interface units as well. The status board computer may comprise a second display screen that is operable in a first mode to display, for more than one patient, information regarding the patient, staff location, bed data, and room status. The status board computer may be located away from the nurse's stations in some embodiments.

The second display screen, when being operated in the first mode, may also display for more than one patient one or more of the following: the position of multiple bed siderails; graphical indicia indicating whether a bed exit alarm is activated; a timer indicating the amount of time that has elapsed since a caregiver has last entered each of the rooms of the more than one patient; and head of bed angle data. The head of bed angle refers to the angle at which a head section of a bed frame is pivoted upwardly with respect to another bed frame portion or with respect to horizontal.

In some embodiments, the nurse call computer and/or the status board computer are communicatively coupled to the plurality of interface units via a network switch and/or via a Power over Ethernet (PoE) switch. However, in other embodiments, other network components or even dedicated cabling may be used to interconnect the nurse call computer and/or status board computer to the plurality of interface units. The communicative coupling may include wired communicative couplings and/or wireless communicative couplings.

According to this disclosure, the second display screen may be operable to display a safety alert history for a selected one of the patients. The safety alert history may include a date and a time at which any siderails of the patient bed associated with the selected one of the patients has been lowered. Alternatively or additionally, the safety alert history may include a date and a time at which any bed exit alerts from the patient bed associated with the selected one of the patients has been generated. Further alternatively or additionally, the safety alert history may include a date and a time at which a caster brake of the patient bed associated with the selected one of the patients has been released.

The second display screen may be operable to display various history screens. For example, the second display may be operable to show a date and a time during which the patient bed associated with a selected one of the patients has been in one or more of the following: a chair mode; a continuous lateral rotation therapy (CLRT) mode, a percussion and vibration therapy (P-V) mode. Alternatively or additionally, the second display screen may be operable to display a weight history for a selected one of the patients to show a date, a time, and a weight reading made by a scale system of the patient bed associated with the selected one of the patients.

With regard to the history screens, the bed status computer may begin gathering the history data for each patient in response to the bed status computer receiving admission information from an Admission Discharge and Transfer (ADT) system and the bed status computer may terminate gathering the history information for each patient in response to the bed status computer receiving discharge information from the ADT system. In some embodiments, the history data associated with the history screens may be transmitted to an electronic medical records (EMR) system by the bed status computer or the nurse call computer or by some other computer device.

In some embodiments contemplated by this disclosure, the second display screen when operating in the first mode may show information regarding those patients only for whom an alert or nurse call has been generated. In such embodiments, for each patient for whom an alert or nurse call has been generated, the second display screen may show an alert/call type and an elapsed time since the alert or nurse call was generated. The alert/call type may comprise, for example, one of a safety alert call type, a normal call type, and a code blue call type.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION OF THE DRAWINGS

The present disclosure relates to the addition of a status board computer 10, and optionally, an enlarged status board display screen 12, to a nurse call system, such as for example, the nurse call system described in U.S. Patent Application Publication Nos. 2009/0212956 A1 and 2009/0217080 A1 which are both hereby expressly incorporated by reference herein. The nurse call system described in U.S. Patent Application Publication Nos. 2009/0212956 A1 and 2009/0217080 A1, as well as the nurse call system described herein, pertains to the NaviCare® Nurse Call™ system marketed by Hill-Rom Company, Inc. As will be described in further detail below in connection with FIGS. 3 and 11, the status board computer 10 and enlarged status board display screen 12, if present, provides at one location dynamic information regarding active calls, patient information, staff location, bed status, and/or room status. This information is presented for all of the rooms within one or more hospital units so that information about an entire unit or multiple units is presented to caregivers at a glance.

Figure 1:
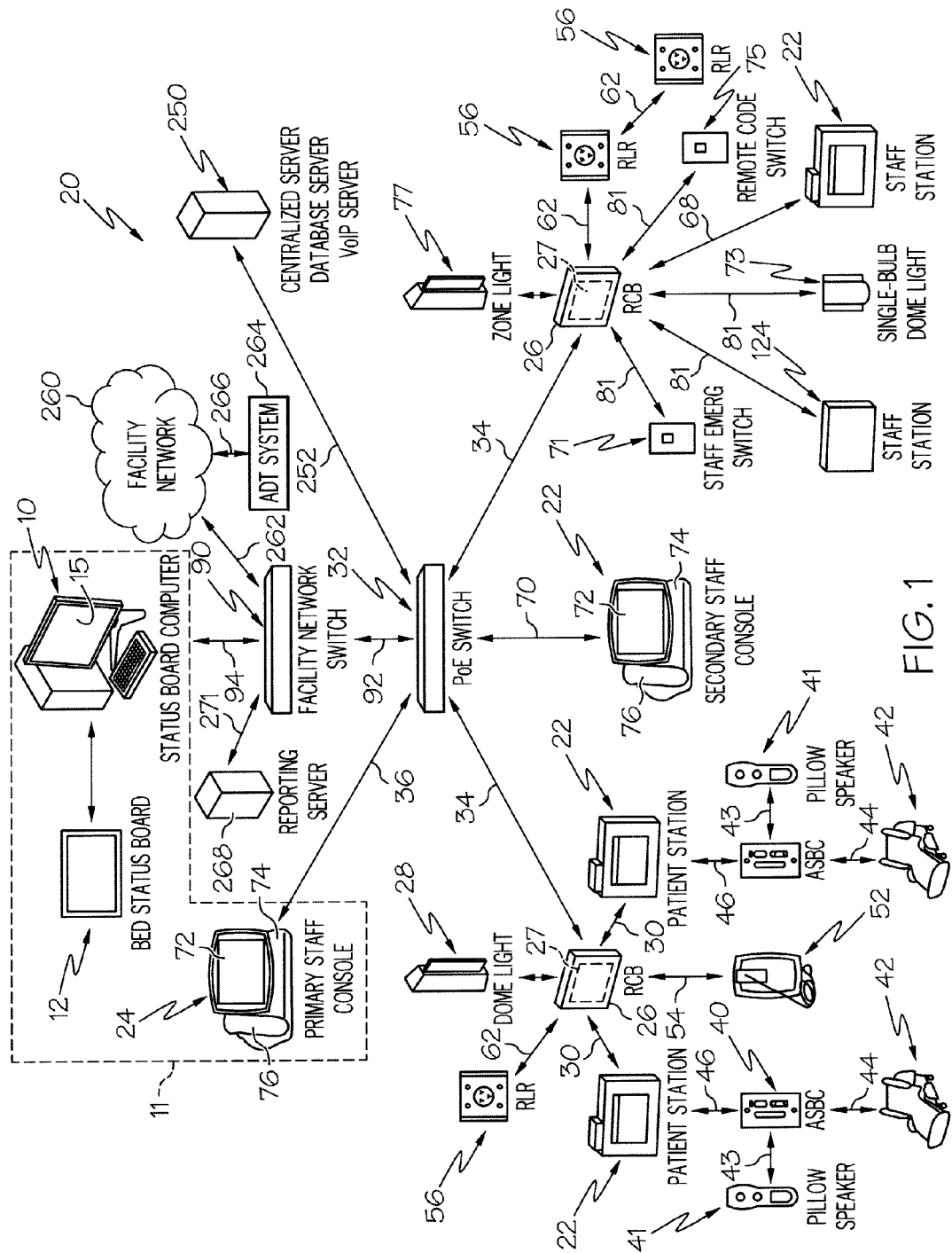
FIG. 1 is a block diagram of a healthcare information system according to this disclosure showing within a dotted L-shaped box a nurse call computer referred to as a primary staff console and a status board computer, each of which is communicatively coupled to multiple hospital beds.

According to one embodiment according to this disclosure, a healthcare communication system 20 which includes bed status computer 10 also includes a plurality of graphical audio stations 22 and a master station or console 24 which are communicatively coupled as shown diagrammatically in FIG. 1. Many of the stations 22 are located in patient rooms and are mounted, for example, to a wall of the respective room or to a headwall unit that, in turn, is mounted to a wall of the respective room. Stations 22 may be mounted to other architectural support structures, such as service chases or columns just to name a couple. Stations 22 may be located in other areas of the healthcare facility as well, such as in staff work areas including, for example, hallways and staff lounges. The stations 22 located in patient rooms may sometimes be referred to herein as patient stations 22, whereas the stations 22 located in staff work areas may be sometimes be referred to herein as staff stations 22. The functionality of stations 22 described herein is applicable to all stations 22 regardless of whether the station 22 is a patient station 22 or a staff station 22, unless specifically noted otherwise.

Patient stations 22 communicate bidirectionally (e.g., two-way communication) with a room control board (RCB) circuit 27 which is located within a housing 26 mounted near a dome light assembly 28. RCB circuit 27 is sometimes referred to as an input/output (I/O) circuit. The bidirectional communication is indicated diagrammatically in FIG. 1 by double headed arrows 30. In the illustrative example, two patient stations 22 are located in the same hospital room and communicate with a single associated RCB circuit 27. Dome light assemblies 28 are typically mounted outside respective patient rooms near the doorways of the rooms and are readily visible to caregivers in the hallway to determine whether any calls or other events indicated on the dome light are occurring within the associated room. Thus, housings 26 with I/O circuit 27 therein are mounted generally at these same locations outside patient rooms in some embodiments. However, having housings 26 mounted elsewhere and spaced from dome light assemblies 28 is within the scope of this disclosure.

In one embodiment, dome light assembly 28 is, for example, an International Business Machines (IBM) Part No. 43T1899 dome light fixture and I/O circuit 27 is, for example, an IBM part no. 43T2063 IO Board. These IBM part nos. are made specifically for Hill-Rom to be marketed as part of the NaviCare® Nurse Call™ system. I/O circuit 27 may sometimes be referred to as an I/O board or an I/O circuit board. However, this is not to imply that all circuit components of the circuitry of I/O circuit 27 need to be on a single circuit board, but that is certainly one possibility. Thus, in some contemplated embodiments I/O circuitry 27 may be distributed among numerous circuit boards, and in other contemplated embodiments some or all of the components of circuit 27 may not be on any circuit board at all. While illustrative circuit 27 is located in housing 26, it is within the scope of this disclosure for various components of circuit 27 to be located in separate housings.

The I/O circuit 27 communicates bidirectionally with a Power over Ethernet (PoE) switch 32 as indicated diagrammatically in FIG. 1 by double headed arrow 34. PoE switch 32 communicates bidirectionally with master station 24 as indicated diagrammatically by double headed arrow 36. Suitable PoE switches are available from a variety of suppliers and may include, for example, the PoE switch marketed by Hill-Rom Company, Inc. in connection with its NaviCare® Nurse Call™ system or such as one or more of the various Dell PoE switches marketed under the PowerConnect™ brand name. While only one patient station 22 is shown in FIG. 1 as being communicatively coupled to master station 24, via the I/O circuit board 27 of assembly 28 and via PoE switch 32, it will be appreciated that system 20 may have numerous such patient stations 22 that may communicate with master station 24 via respective I/O circuit boards 27 and via PoE switch 32.

As indicated diagrammatically by dotted L-shaped box 11 in FIG. 1, it is contemplated by this disclosure that bed status computer 10 and master console 24 are co-located together at the master nurse call station. However, it is also within the scope of this disclosure for the bed status computer 10, as well as the enlarged bed status display screen 12 if there is one, to be located away from the master nurse station at which master console 24 is located. For example, bed status computer 10 may be located within a hospital administrator's office.

In some embodiments, such as the one shown in FIG. 1, system 20 includes bed connector units 40, each of which is communicatively coupled to an associated hospital bed 42 as shown diagrammatically in FIG. 1 via lines 44. Bed connector units 40 are, in turn coupled to respective patient stations 22 as indicated diagrammatically in FIG. 1 via lines 46. Other arrangements for interconnecting beds 42 with the associated master console 24 are described in U.S. Patent Application Publication No. 2009/0212956 A1 which is already incorporated by reference herein. In some embodiments, beds 42 comprise one or more of the beds marketed by Hill-Rom Company, Inc. under the brand names TOTALCARE®, VERSACARE®, ADVANCED-1000™, CCUII™ and ADVANTA™. The illustrative bed connector units 40 are also configured to connect to handheld pillow speaker units 41 as indicated diagrammatically via lines 43.

Figure 2:
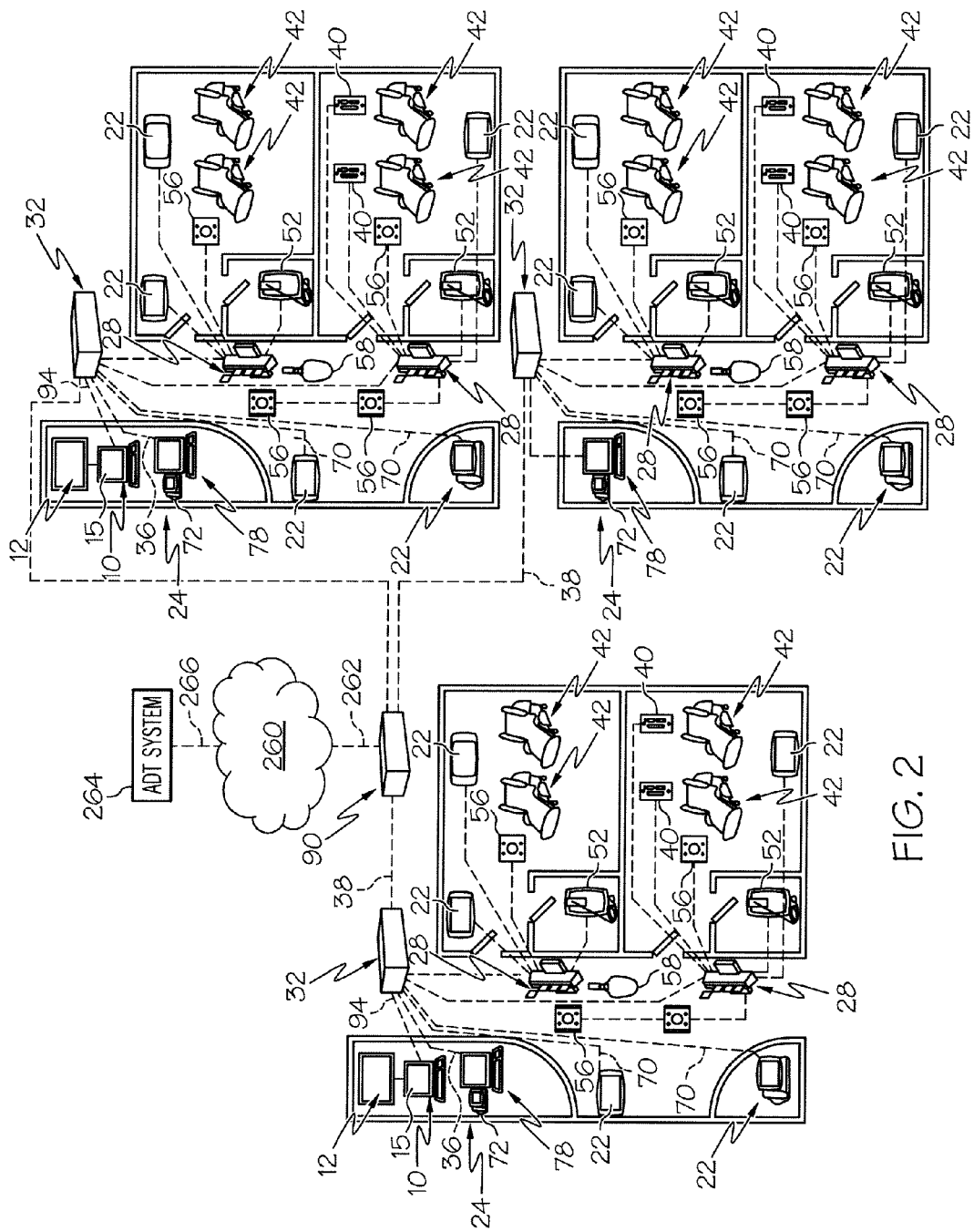
FIG. 2 is block diagram showing various nursing units of a healthcare facility having nurse call computers and status board computers located at master nurse stations of each of the nursing units and communicatively coupled to each other and coupled to other computer devices of a network of the healthcare facility.

Typically, all of the patient stations 22 of a nursing unit communicate with the same master station 24. The master stations 24 and graphical audio stations 22 of different nursing units may be coupled together by interconnecting the respective PoE switches 32 as indicated diagrammatically in FIG. 2 via dotted lines 38. The illustrative example of FIG. 1 includes a facility network switch 90 that communicates bidirectionally with PoE switch 32 as indicated diagrammatically via line 92. Facility network switch 90 is shown in FIG. 2 as being coupled to the PoE switches 32 of the various nursing units. Thus, information can be shared, and communications established, between computer devices, such as stations 22, 24, of different nursing units.

According to this disclosure, if desired, the bed status computer 10 located at one nursing is able to display data pertaining to other nursing units. In the diagrammatic embodiment of FIG. 2, for example, two of the nursing units have bed status computers 10, each with an associated enlarged bed status board display 12, and one of the nursing units does not have any bed status computer 10 or associated display 12. The two bed status computers 10 each communicate with an associated PoE switch 32 as indicated by dotted lines 94. However, it should be understood that both of the bed status board computers 10 are able to receive an display data from any of the three nursing units that are illustrated in FIG. 2. Accordingly, it is not necessary that each and every nursing unit of a healthcare facility have a bed status computer 10 although that is certainly within the scope of this disclosure. In other systems, bed status computers 10 may not communicate with associated PoE switches, but instead may communicate directly with the facility network switch 90. Such an alternative is shown in FIG. 1 in which bed status computer 10 communicates bidirectionally with facility network switch 90 as indicated diagrammatically with line 94.

Many other types of devices in a patient room may also couple to a respective I/O circuit 27 mounted near the corresponding dome light assembly 28 to communicate with master station 24 and, if desired, other computer devices of the a computer network of the healthcare facility. For example, in FIG. 1, a wall-mounted nurse call switch 52 which may be mounted in a lavatory of the patient room, for example, is coupled to the circuit board 27 of assembly 28 as indicated diagrammatically by double-headed arrow 54. Furthermore, a wireless receiver 56, which illustratively is an infrared receiver that receives wireless signals from locating-and-tracking badges 58, shown in FIG. 2, worn or carried by caregivers is coupled to the I/O circuit 27 as indicated diagrammatically by double-headed arrow 62 as shown in FIG. 1. Wireless receivers 56 are sometimes referred to as room location receivers (RLR). In one of the examples given in FIG. 1, RLR's 56 are daisy chained together such that one of the RLR's 56 communicates with circuit 27 via another of the RLR's 56.

As previously mentioned, some graphical audio stations 22 are located in staff work areas and are referred to as staff stations or consoles 22. In FIG. 1, a first staff station 22 communicates bidirectionally with an associated RCB circuit 27 via a communications link 68 and a second staff station 22 communicates bidirectionally directly with PoE switch 32 via a communications link 70. The first staff station 22 is mounted to a wall, for example, whereas the second staff station 22 has a graphical display screen module 72 connected to a base module 74 which includes a telephone hand set 76. The master station 24 shown in the FIG. 1 example also has a graphical display screen module 72 connected to a base module 74 which has a telephone handset 76. In the FIG. 1 example, the first staff station 22 is in communication with PoE switch 32 via the RCB 27 and associated communication link 34.

Some further exemplary devices coupled to RCB circuit 27 in the FIG. 1 example include a staff emergency switch 71, a simplified staff station 124 (aka a Standard Room Station or SRS), a single-bulb dome light 73, a remote code switch 75, and a zone light 77. Each of these further devices 71, 73, 75, 77, 124 is shown communicating bidirectionally with RCB 27 via diagrammatic lines 81. In some embodiments, master consoles 24 and staff consoles 22 having display 72 coupled to base 74 are model number GRS-10 devices available from Hill-Rom Company, Inc. Also in some embodiments, patient stations 22 and staff stations 22 that are not coupled to base 74 are model number GRS-5 devices available from Hill-Rom Company, Inc. The simplified staff station 124 may be IBM part no. 43T2082 which is available from Hill-Rom Company, Inc. as model number SRS.

The FIG. 2 example shows that a personal computer 78 may cooperate with the associated display screen module 72 to provide the master station functionality. In other embodiments, personal computer 78 is the only computer device included in master station 24 while, in still other embodiments such as the one of FIG. 1, personal computer 78 is omitted. Thus, depending upon the manner in which a graphical display module 72 is programmed it can serve as a patient station 22, a staff station 22 or as a master station 24. When serving as a staff station 22 or a master station 24, module 72 can be coupled to base module 74, if desired. The display screen of module 72 is approximately a 10 inch display screen in some embodiments and therefore is larger than the LCD screen used in, for example, the COMLINX® system.

Each of the communications links 30, 34, 36, 38, 44, 46, 54, 60, 62, 66, 68, 70, 81, 92, 94 shown diagrammatically by lines or arrows in FIGS. 1 and 2, as well as any other communications links described herein, may include wired links and/or wireless links and/or combinations thereof, along with associated connectors. For example, with regard to links 44 between beds 42 and bed connector units 40, known cables having 37-pin connectors (or similar connectors) may provide these links 44. Alternatively or additionally, some of links 44 may be wireless links, in which case, the respective beds 42 and units 40 have appropriate wireless transmitter and wireless receiver circuitry, which may be in the form of a wireless transceiver. Such wireless communication between beds 42 and units 40 is discussed, for example, in U.S. Pat. No. 7,319,386 and in U.S Patent Application Publication No. 2007/0210917 A1, both of which are hereby incorporated herein by this reference.

It is also contemplated that the communication protocol for links 30, 34, 36, 38, 44, 46, 54, 60, 62, 66, 68, 70, 81, 92, 94 may be according to any suitable protocol such as the TCP/IP protocol, the RS-232 protocol, the RS-422 protocol, the RS-423 protocol, or the RS-485 protocol, or similar such protocols, and such as wireless protocols including any of the IEEE 802.11$_x$ protocols (where x represents the various revision levels a, b, c, d, e, g and so forth of the 802.11 protocol), the Bluetooth protocol, the Zigbee protocol, or similar such wireless communication protocols. In some embodiments, the Palmetto protocol described in U.S. Patent Application Publication Nos. 2009/0212956 A1 is used as the communication protocol for the data sent one or more links 30, 34, 36, 38, 44, 46, 54, 60, 62, 66, 68, 70, 81, 92, 94.

In one embodiment, for example, links 30, 44, 46, 54, 62, which are the communications links associated with a patient room that communicate between devices in the patient room and the I/O circuit board 27 of dome light assembly 28, are according to the RS-485 protocol, whereas links 34, 36, 68, 70, 92 which are the links to and from PoE switches 32, are according to the TCP/IP protocol. The devices that communicate over these various links are configured and programmed appropriately for the required RS-485 or TCP/IP protocol, as the case may be.

As to the various devices coupled to I/O circuit 27 other than stations 22, in some embodiments, the circuitry of I/O circuit 27 operates to convert the data from these various devices according to their device-specific communication protocols (e.g., serial links to stations 124; locating and tracking receivers 56 room bus protocol; bed connector 40 room bus protocol; and serial to dome light protocol) into the TCP/IP protocol for subsequent transmission to the PoE switch and ultimately to the master station 24 and to other network devices, if desired.

While stations 22, 24 each have graphical displays, stations 124 are a low cost offering that don't have any graphical display but that provide call cancel, call placement, reception for signals from locating badges 58 and voice communication functionality. Stations 124 connect to the I/O circuit board of assembly 28 via an RS-485 connection. Stations 124 can be configured as a patient station, staff station, or visitor station.

According to this disclosure, the components of system 20 which cooperate to provide a healthcare facility with a nurse call system are referred to collectively as a "base nurse call system." Thus, stations 22, 122 and I/O circuit 27, dome light assemblies 28, and any of the equipment described above that is capable of providing a nurse call signal, as well as the associated master station 24 and PoE switches 32 along with any of the communication links interconnecting these components, are among the components which comprise a "base nurse call system" according to this disclosure. Staff stations 22, if present, are also considered to comprise part of the base nurse call system.

Base nurse call systems are subject to Underwriter's Laboratories UL-1096 requirements. According to some embodiments contemplated by this disclosure, the bed status board computer 10 and, if present, the associated enlarged bed status board display screen 12 are not part of the base nurse call system and so are not subject to the UL-1096 requirements. However, the bed status board computer 10 and optional screen 12 provide caregivers with some of the same information that the base nurse call system provides to caregivers. In this regard, some of the information displayed on the monitor of bed status board computer 10 and/or screen 12 is redundant to information that may be displayed on screen 72 of master station 24. While the components of the base nurse call system of illustrative system 20 are compliant with the Underwriter's Laboratories 1069 standard according to this disclosure, this is not to imply that the components of the base nurse call system may not also be compliant with other standards relating to nurse call systems or relating to some other aspect of these devices.

According to other embodiments contemplated by this disclosure, the bed status board computer 10 and, if present, the associated enlarged bed status board display screen 12 are part of the base nurse call system and so are compliant with UL-1096 requirements. In some of such embodiments, the bed status computer 10 is coupled to the same PoE switch 32 that the master console 24 rather than being coupled to the network facility switch 90. If desired, the reporting server 268 may also be coupled to the PoE switch 32 rather than the facility network switch 90. It is contemplated by this disclosure that the functionality of status board computer 10 and master console 24 can be merged into a single computer device. For example, status board computer 10 may be configured to permit a nurse at the master station to answer nurse calls via the status board computer 10 and master console 24 may, in turn, be omitted. Such a capability is facilitated at computer 10, in some embodiments, by use of voice over Internet Protocol (VoIP) communications technology and software.

If voice communication capability among stations 22, 24, 124 is to be a function of the nurse call system, then a Voice over Internet Protocol (VoIP) sever 250 is also included in the base nurse call system and is coupled to PoE switch 32 via a TCP/IP communications link 252 as shown diagrammatically in FIG. 1. Server 250 facilitates communication between which ever of stations 22, 24, 124 are present in the system 20. Server 250 is configured to translate system operations and communications to the corresponding messages that then control endpoint devices, such as stations 22, 124, consoles 24, or room input/output circuits 27. As such, server 250 may include a soft telephony switch and other associated components in some embodiments. Server 250 may also provide integration with the hospital telecommunications structure (not shown), although some other server may do so as well.

As shown diagrammatically in FIG. 1, the healthcare communication system 20 includes a facility network or Ethernet 260 that communicates with facility network switch 90 via a bidirectional communications link 262. Facility network 260 includes all of the various other computer devices (not shown), hardware (not shown), and software (not shown) that those skilled in the art typically consider as comprising an Ethernet of a healthcare facility. Furthermore, the components shown in FIGS. 1 and 2 such as computer 10, stations 22, 24, 124, RCB 27, server 250 are also considered to be part of the facility network of system 20. In other words, the facility network 260 "cloud" shown in FIGS. 1 and 2 is intended to be representative of all of the parts of any given healthcare system 20 that are not specifically described herein.

In the illustrative example of FIG. 1, an admission, discharge, and transfer (ADT) system 264 is shown communicating via a bidirectional communications link 266 with facility network 260. In some embodiments, bed status computer 10 receives patient information from the ADT system 264 via network 260, network switch 90, and the associated communications links 92, 94, 262, 266. Also in the illustrative example, a reporting server 268 is coupled to facility network switch 90 via a bidirectional communications link 271. In the illustrative embodiment, the reporting server 268 serves as a data repository for bed data emanating from patient beds 42 and bed status computer 10 obtains data from the reporting server for populating the information on the various screens shown in FIGS. 3-10, for example. Reporting server 268 may receive data from other sources, such as for example, an Electronic Medical Records (EMR) system in some embodiments, and reporting server 268 may be included as part of an EMR system in some embodiments.

While the term "server" is used herein, it will be understood by those skilled in the art that the functionality represented or performed by devices referred to as "severs" may comprise and be performed by any suitable computer device having software programs or services that may be resident and/or executable by any computer, device or equipment in the system or more than one computer, device or equipment in the network. Thus, there term "server" is intended to broadly encompass any computer device that is capable of performing the mentioned functions.

Figure 3:
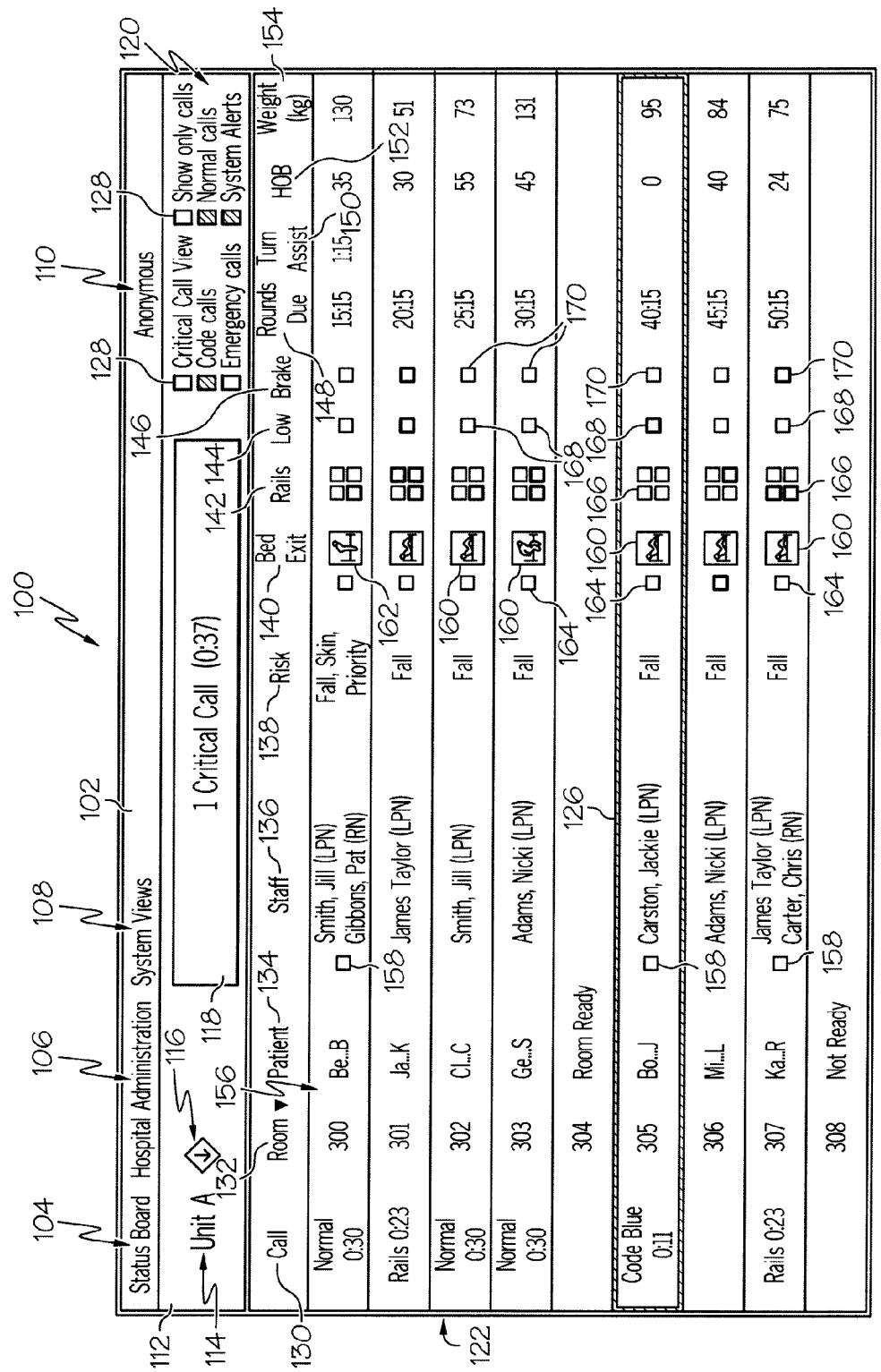
FIG. 3 is a screen shot of an example of a status board screen shown on a display of the status board computer showing for each room in the associated nursing unit information about the patient of each room, the staff assigned to each of the patients, and the status of the hospital bed associated with each of the patients.

Referring now to FIG. 3, an example of a status board screen 100 which is shown on a display or monitor 15 of the status board computer 10 includes a header bar 102 that has a Status Board icon 104, a Hospital Administration icon 106, a System Views icon 108 and an Anonymous identifier 110. Header bar 102 is shown on display 15 at all times that the bed status computer system is operating to permit the user to navigate to the main portion of the system. Thus, when Status Board icon 104 is selected, computer 10 responds with status board screen 100 which is discussed in further detail below.

When Hospital Administration icon 106 is selected, computer 10 responds with an administration screen (not shown) that permits a hospital administrator to enter a user name and password to gain access to various other screens to set up new users of the system, for example. In some embodiments, such other screens also permit the administrator to add caregivers to the list of assignable caregivers and to assign particular caregivers to patients and/or to rooms in the nursing unit. In other embodiments, the caregiver assignments to patients and/or rooms are made using the associated master console 24 and then that data is communicated to bed status computer 10 so that the assignment information can be properly shown on screen 100.

When System Views icon 108 is selected, computer 10 responds with the types of screens which are shown, for example, in FIGS. 4-9 and which are discussed in further detail below. The Anonymous identifier 110 shown in header bar 103 simply indicates that the a user with the user name "Anonymous" has logged into the bed status system which includes computer 10. Thus, when a user having a user name established within the bed status computer system, then the Anonymous identifier 110 is replaced under such circumstances by the particular user's user name.

In the illustrative status board screen 100, a display control area bar 112 appears beneath header bar 102 but above a main table 122. Illustrative display control area bar 112 includes a Unit A identifier 114, a Unit Selector icon 116, a Dynamic Message Area box 118, and a Calls Selection menu 120. The Unit A identifier 114 in the illustrative example indicates the user has selected to view the data associated with Unit A. If the user selects the Unit Selector icon 116, then computer 10 responds with a drop down menu in the vicinity of icon 116 that has a list of the nursing units that may be view on status board screen 100. For example, such a drop down menu may include a list such as Unit A, Unit B, Unit C, All Units. The user then selects in the drop down menu the unit or units for which the user desired the data to be displayed on screen 100.

The Dynamic Message Area box 118 shows any calls that have been received from any of the rooms in the nursing unit or units selected using icon 116. If there are multiple calls and multiple call types, then the calls are prioritized and appear in Dynamic Message Area box 118 in the following manner. More specifically, if more than one call exists, the viewable message in box 118 will rotate using a vertical scrolling marquee technique. In connection with scrolling through the calls, each message will be visible for a threshold amount of type, such as about 8 seconds in one embodiment, before rotating out to show the next message. However, if one or more code call exists, then the list of messages that appear in box 118 are limited to the code call(s). Code calls typically are made when a patient goes into cardiac arrest.

If there are no code calls, but one or more emergency calls exist, then the list of messages that appear in box 118 are limited to the emergency call(s). Once all code and emergency calls have been canceled, then the scrolling of regular calls or normal messages appears in box 118 on a rotating or scrolling basis as mentioned above. In some embodiments, System Alert calls which relate to, for example, an error condition in a piece of equipment, do not count toward the total number of calls and are not displayed in box 118. In other embodiments, the System Alert calls are shown in box 118 along with the regular or normal calls. Similarly, in some embodiments, Bed Disconnect alerts which indicate that a bed 42 has been disconnected from its respective bed connector unit 40, do not count toward the total number of calls and are not displayed in box 118. In other embodiments, the Bed Disconnect alerts are displayed in box 118 along with the regular or normal calls.

It is contemplated by this disclosure that the amount of time that has elapsed since a particular call has been placed can be included in box 118 during the time that the associated call or alert is displayed in box 118. For example, in FIG. 3, the message "1 Critical Call (0:37)" appears in box 118 to indicate that 37 seconds have elapsed since the critical call was placed. In the FIG. 3 example, the Critical Call is a Code Blue call from room 305 as indicated by highlighting 126 around the associated line in the main table 122 of screen 100. The text "Normal—Cardiology, Room 101 has been waiting for 32:45 min" is another example of the type of information that may be displayed in box 118 in some embodiments. In this second example, a normal call has been placed by the patient in room 101, which happens to be in the Cardiology unit of the healthcare facility, and 32 minutes, 45 seconds have elapsed since the patient in room 101 placed the normal call. Based on the foregoing, it should be understood that the particular text used for a particular type of call shown in box 118 is at the discretion of the system programmer and may even be configurable by a hospital administrator such that the couple examples given herein are intended to be illustrative of the basic idea.

In some embodiments, the amount of time that has elapsed is referred to as a Call Threshold Indicator and may be a number that is preprogrammed or that is preselected by a hospital administrator. For example, a Call Threshold Indicator may be set at 15 minutes. Thus, after a call occurs, the elapsed time since the call is not displayed in box 118 until after the threshold amount of time has elapsed. After the threshold amount of time has elapsed, which in the given example is 15 minutes, then the time since the call was placed is indicated in box 118.

Calls selection menu 120 includes a set of choices that are selectable by the user of computer 10 to indicate which types of calls and/or alerts are to be shown within box 118. In the illustrative example of FIG. 3, menu includes the following choices: "Critical Call View;" "Code Calls;" "Emergency Calls;" "Show Only Calls;" "Normal Calls;" and "System Alerts." An indicator box 128 appears next to each choice of menu 120. In the illustrative example, indicator boxes 128 associated with the "Code Calls;" "Normal Calls;" and "System Alerts" menu items are filled in to indicate that the user has selected these types of calls to appear in box 118. It should be apparent from FIG. 3 that the main table 122 indicates all of the types of calls that may occur in any of the rooms in the unit such that the information appearing in box 118 is redundant to information that otherwise can be seen on main table 122.

Main table 122 occupies the majority of screen 100 and includes rows that correspond to each room in the nursing units that have been selected via icon 116 for display. In the illustrative example in which Unit A is the only nursing unit chosen for display, there is a row for each room 300-308 that is included in the nursing unit. If there are more rooms in a nursing unit than are able to fit onto the viewing area of main table 122, then a scroll bar appears at the left or right side of table 122 to permit the user to scroll down to see the additional rooms. Main table 122 includes the following columns of information: a Call column 130; a Room column 132; a Patient column 134; a Staff column 136; a Risk column 138; a Bed Exit column 140; a Rails column 142; a Low column 144; a Brake column 146; a Rounds Due column 148; a Turn Assist column 150; a Head of Bed (HOB) column 152; and a Weight (kg) column 154.

Call column 130 shows the type of call, if any, that has been placed or that has otherwise been detected for each room in the unit. Next to or beneath the text indicating the type of call is a clock in minutes:seconds format to indicate the amount of time that has elapsed since the associated call was placed or detected. In the illustrative example, Normal calls were placed from each of rooms 300, 302, and 303 thirty seconds ago, Rails call were detected in rooms 301 and 307 twenty-three second ago, and a Code Blue call was placed from room 305 eleven seconds ago. It should be understood that the illustrative example provides a somewhat unrealistic scenario in that it is unlikely that patients in three rooms would place a Normal call, such as by pressing the nurse call button on a bed siderail or on a pillow speaker, at exactly the same time and it is unlikely that patients or caregivers in two rooms would lower one or more bed siderails at exactly the same time. It should be noted that, in the illustrative example, no calls of any type exist with regard to rooms 304, 306 and 398.

The Room column 132 shows the number of the room associated with each row of information. An ascending/descending sort icon 156, illustratively a triangle, appears next to the word "Room" in the column 132 heading. Icon 156 can be selected to change the sort from ascending to descending and vice versa. In the illustrative example, the room numbers are sorted into ascending order. That is, the room numbers go up from 300 to 308 down the table 122. If the room numbers were sorted in descending order, they would go down from 308 to 300 down the table. As will discussed below in connection with the FIG. 10 example, other sorting techniques for the data appearing on monitor 15 of computer 10 and/or on display screen 12 are contemplated by this disclosure. In those situations in which hospital rooms have two patients located therein, then Room column 132 includes either "A" and "B" indicators appended to the two-patient room numbers (e.g., 101A and 101B) or "-1" and "-2" indicators appended to the two-patient room numbers (e.g., 101-1 and 101-2) or some similar such nomenclature scheme.

The Patient column 134 shows, for each of the rooms that contain a patient, a patient identifier in a HIPAA compliant format. In the illustrative example, a partial patient name is shown by indicating the first two letters of the patient's last name followed by a set of ellipses and the first letter of the patient's first name. In the illustrative example, the row associated with room 304 has the text "Room Ready" in the Patient column 134. This indicates that no patient is in the room currently but the room is ready to receive a patient. Also in the illustrative example, the row associated with room 308 has the text "Not Ready" in the Patient column 143. This indicates that there is no patient in the room currently and that the room is not yet ready to receive a patient. To indicate that a room is ready to receive a patient, a caregiver may enter certain information on the patient station 22 located in the associated patient room as discussed in further detail in U.S. application Ser. No. 12/708,891, filed Feb. 19, 2010, which is titled "Patient Room and Bed Management Apparatus and System" and in U.S. application Ser. No. 12/711,912, filed on the same date as the present application, which is also titled "Patient Room and Bed Management Apparatus and System" and both of which are hereby expressly incorporated by reference herein. Alternatively or additionally, the user can change the status of a particular room from "Not Ready" to "Room Ready" using the bed status computer 10.

The Staff column 136 lists the names of the caregivers who are assigned to patients in each of the rooms. As can be seen in FIG. 3, some patients have two assigned caregivers and others only have one assigned caregiver. In the illustrative example, the caregiver names are listed in last name, first name format. A parenthetical abbreviation follows the caregiver name to indicate the caregiver's role. For example, RN is the abbreviation for registered nurse and LPN is the abbreviation for licensed practical nurse. Staff column 136 also includes an icon 158, illustratively a square, to indicate whether or not a caregiver is present in the patient room. In the example of FIG. 3, caregivers are present in rooms 300, 305, and 307. Thus, computer 10 receives information form a locating and tracking system of the healthcare facility in order to determine whether icon 158 is to be shown on screen 100 in the Staff column 136 of a particular row. The locating and tracking system includes, for example, badges 58 and room locating receivers 56 which are described above. The locating and tracking information is stored in reporting server 268 in some embodiments.

The Risk column 138 indicates within each row of table 122 whether the associated patient has been identified as having a particular type of risk. In the illustrative example, patients in rooms 301-303 and 305-307 have each been identified as having a "Fall" risk. If a patient is considered a Fall risk, then typically it is not desirable for that patient to get out of bed unless a caregiver is present in the room to assist the patient. Accordingly, for Fall risk patients, an alert condition will be considered to exist if any of the bed siderails are moved to a lowered position or if the patient exits the bed. Also in the illustrative example, the patient in room 300 has been identified as having a "Fall" risk, a "Skin" risk, and a "Priority" risk. Thus, bed status computer 10 is able to indicate multiple risk types on table 122 for particular patients if necessary. A patient indicated as a "Skin" risk, then this typically means that the patient has a higher than normal risk of developing bed sores or pressure ulcers. A patient identified as a "Priority" risk means that the patient likely requires more nursing attention than other patients on the unit. The information indicating that a patient is a particular risk type may come from a number of sources. For example, the information may be entered by a user of computer 10 in some instances and may be transmitted to computer 10 and/or reporting server 268 from another portion of system 20 such as ADT system 264 or an EMR system. Thus, in some embodiments, the Risk column 138 of table 122 may be auto-populated with risk data that originates from another portion of system 20.

According to this disclosure, in some embodiments, the risk names such as Falls and/or Lungs, are color coded to indicate whether or not safety monitoring associated with the particular risk is turned on at the associated bed 42. For example, a color coding of green means that the associated monitoring is turned on, a color coding of yellow means that the associated monitoring is turned off, and a color coding of red means that at least one of monitored conditions associated with the particular risk name is alarming. It is contemplated by this disclosure that beds 42 may have a button or other user input to turn the safety alerting on, to turn the safety alerting off, and/or to suspend or silence the safety alerting. Alternatively or additionally, a user input to turn the safety alerting on and/or off, or to suspend or silence the safety alerting, may be provided on patient stations 22. For example, patient stations 22 may have one or more touch screen buttons for one or more of these purposes.

The Bed Exit column 140 indicates whether or not a bed exit system of the hospital bed 42 associated with the patient of each row of table 122 is armed, at what level it is armed, and whether a bed exit alarm is occurring. In the illustrative example, there are three levels of bed exit sensitivity that can be chosen when the bed exist system of a particular bed 42 is armed. Those levels are patient position mode, bed exiting mode, and out-of-bed mode. When the bed exit system of an associated patient bed 42 is armed in the patient position mode, then a patient position mode icon 160 appears in column 140 as shown in table 122 with regard to rooms 301, 302 and 305-307. When the bed exit system of an associated patient bed 42 is armed in the bed exiting mode, then a bed exiting mode icon 162 appears in column 140 as shown in table 122 with regard to room 303. When the bed exit system of an associated patient bed 42 is armed in the out-of-bed more, then an out-of-bed mode icon 164 appears in column 140 as shown in table 122 with regard to room 300.

Column 140 also includes an alarm on/off indicator 164, illustratively a square, to indicate whether or not a bed exit alarm is occurring. If a bed exit alarm is occurring, then the alarm on/off indicator 164 becomes highlighted as shown in table 122 with regard to room 306, for example. The data shown in column 140 is based on information transmitted from the beds 42 located in the patient rooms of the nursing unit for which the information viewed on monitor 15 and/or display screen 12 is associated. The bed exit systems are typically armed by caregivers at the bedside by manipulating the appropriate bed exit user interface devices, such as buttons or touch screen, found on the individual beds. However, it is within the scope of this disclosure for the bed exit systems of beds 42 to be armed via some other user input device or computer device such as stations 22, 24.

The Rails column 142 indicates for each of the hospital beds 42 in each of the patient rooms, whether the siderails of the bed are in a raised position or in a lowered position. In the illustrative example of FIG. 3, four indicators 166 which illustratively are squares are provided in each row with each individual square 166 corresponding to one of the four siderails of the associated hospital bed 42. There are four siderails included on many hospital beds and these four siderails are oftentimes referred to as the left headrail, the right headrail, the left footrail, and the right footrail. In those instances when a particular bed 42 has a different number of siderails, such as having only two siderails for example, then a corresponding number of indicators 166 are provided in column 140. If a particular siderail corresponding to an associated icon 166 in column 142 is lowered, then the icon 166 becomes highlighted as is shown for several of icons 166 in FIG. 3. If a particular siderail corresponding to an associated icon 166 is raised, then the icon 166 remains unhighlighted as is shown for the remaining icons 166 in FIG. 3. The data shown in column 142 is based on information transmitted from the beds 42 located in the patient rooms of the nursing unit for which the information viewed on monitor 15 and/or display screen 12 is associated.

The Low column 144 includes an indicator 168, illustratively a square, for each of the hospital beds 42 in each of the patient rooms which indicates whether an upper frame of the bed 42 is in its lowest position relative to a base frame of the bed 42. If the upper frame of a particular bed is not in its lowest position, then the icon 168 becomes highlighted as is shown for icons 168 associated with rooms 301 and 305 in column 144 of table 122. If the upper frame of a particular bed is in its lowest position, then the icon 168 remains unhighlighted as is shown for the icons 168 associated with rooms 300, 302, 303, 306 and 307 in column 144 of table 122. The data shown in column 144 is based on information transmitted from the beds 42 located in the patient rooms of the nursing unit for which the information viewed on monitor 15 and/or display screen 12 is associated.

The Brake column 146 includes an indicator 170, illustratively a square, for each of the hospital beds 42 in each of the patient rooms which indicates whether the caster brakes of the bed 42 are braked. If the casters of a particular bed are not braked, or to put it another way, if the casters of a particular bed are released, then the icon 170 becomes highlighted as is shown for icons 170 associated with rooms 301 and 307 in column 146 of table 122. If the casters of a particular bed are braked, then the icon 170 remains unhighlighted as is shown for the icons 170 associated with rooms 300, 302, 303, 3065 and 306 in column 146 of table 122. The data shown in column 144 is based on information transmitted from the beds 42 located in the patient rooms of the nursing unit for which the information viewed on monitor 15 and/or display screen 12 is associated.

The Rounds Due column 148 includes, for each row corresponding to a patient in table 122, a countdown timer or clock to indicate when the next rounds are due for the associated patient. In this regard a "round" is considered to be a scheduled visit by an assigned caregiver to the patient's room regardless of whether any call has been placed or any alert condition detected. The countdown timer or clock is illustratively shown in a minutes:seconds format. In the illustrative example, the rounds for each of the patient rooms is scheduled 5 minutes apart. Thus, for room 300, the next round is due in 15 minutes, 15 seconds; for room 301, the next round is due in twenty minutes, fifteen seconds; and so on. The time interval between rounds to a particular patient can be set by the user with computer 10 or can be based on information transmitted from some other portion of system 20 such as the ADT system or EMR system for example. Also, the time allotted for a caregiver to be in a room during the scheduled visit can be set by the user with computer 10 or can be based on information transmitted from some other portion of system 20 such as those mentioned above.

The Turn Assist column 150 includes, for particular rows corresponding to one or more selected patients in table 122, a countdown timer or clock to indicate when the next turn of the patient is to occur. In this regard a turn of patient means rolling the patient from their back to either their right or left side or vice versa, or rolling the patient from their left side to their right side. Some hospital beds 42 have a turn assist function in which a left turn assist bladder or a right turn assist bladder is inflated on a one-time basis for a short period of time to assist a caregiver in turning the patient either toward the left or toward the right as the case may be. The countdown timer or clock in column 150 is illustratively shown in a minutes:seconds format. In the illustrative example, the a turn assist for the patient in room 300 is scheduled to occur in 15 minutes, 15 seconds. The time interval between turn assists of a particular patient can be set by the user with computer 10 or can be based on information transmitted from some other portion of system 20 such as the ADT system, the EMR system, or a computerized physician's order system, for example.

The Head of Bed (HOB) column 152 indicates for each hospital bed 42 associated with a patient of a corresponding row of table 122, the angle at which a head section of the bed is elevated with respect to horizontal or with respect to an upper frame of the bed 42. In the illustrative example, the bed 42 in room 300 has its head section raised by 35 degrees, the bed 42 in room 301 has its head section raised by 30 degrees, and so on. The data shown in column 152 is based on information transmitted from the beds 42 located in the patient rooms of the nursing unit for which the information viewed on monitor 15 and/or display screen 12 is associated.

The Weight (kg) column 154 indicates the weight of each patient associated with a corresponding row of table 122 as measured by a weight scale system of the respective bed 42. In the illustrative example, each of the weights in column 154 is in the units of kilograms. Computer 10 can be used to change the weight units to pounds in some embodiments. The data shown in column 154 is based on information transmitted from the beds 42 located in the patient rooms of the nursing unit for which the information viewed on monitor 15 and/or display screen 12 is associated. The weight scale systems of many beds 42 permit caregivers to select whether the weight measurement is displayed at the bed in pounds or kilograms. Thus, there is a chance that some beds in a unit are set to display weight in pounds and others are set to display weight in kilograms. According to this disclosure therefore, computer 10 is configured to convert weight in pounds to weight in kilograms if column 154 is set to display weight in kilograms and computer 10 is configured to convert weight in kilograms to weight in pounds if column 154 is set to display weight in pounds. In other embodiments, the weights shown in column 154 may have the same units as received from the associated bed 42 in which case, the pounds (lb) or kilogram (kg) units designators appear next to each of the weights in column 154.

Figure 4:
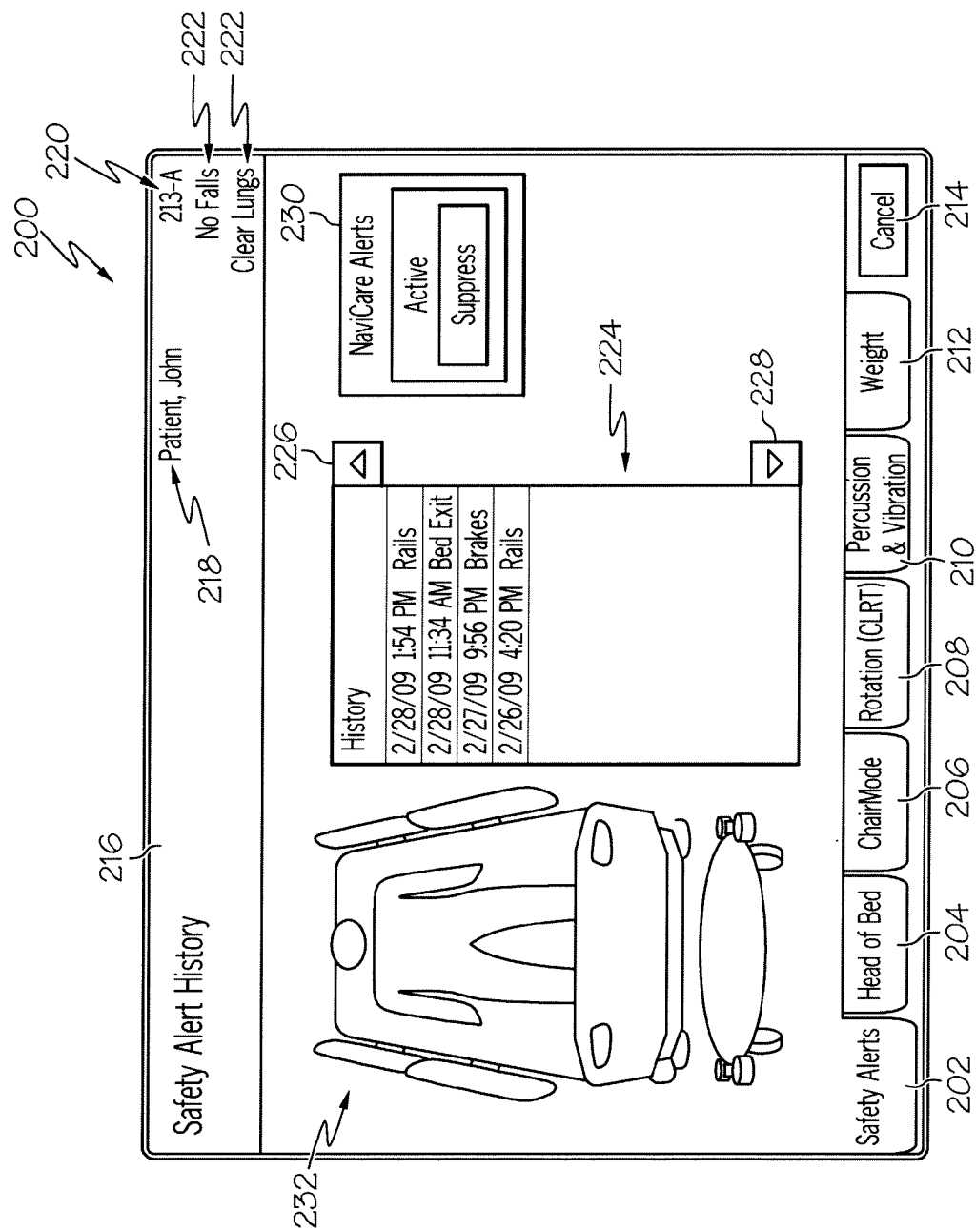
FIG. 4 is a screen shot of an example of a Safety Alert History window.

If a user selects Systems Views icon 108 on screen 100, computer 100 responds with a Safety Alert History window 200 an example of which is shown in FIG. 4. The information in the windows of FIG. 4-9 pertain to the patient associated with the row that the user highlighted or selected on table 122 of screen 100. Window 200 is the default window that appears upon selection of icon 108. Window 200 actually appears over a portion of table 122 such that the header bar 102 and display control area bar 112 can still be seen above window 200 on monitor 15 and/or display screen 12. Along the bottom of window 200 are a Safety Alerts tab 202, a Head of Bed tab 204, a ChairMode tab 206, a Rotation (CLRT) tab 208, a Percussion & Vibration tab 210, a Weight tab 212, and a cancel button 214.

Window 200 has a header area 216 with the "Safety Alert History" title appearing on the left-hand side. Header area 216 also includes the patient's name 218 but not in a HIPAA compliant format. In other embodiments, the patient's name is shown in header area 216 in a HIPAA compliant format. Header area 216 further includes on the right hand side the patient's room number 220 and any risk categories 222 designated for the patient as discussed above. In the illustrative example, the patient's name 218 is John Patient, the patient's room number 220 is 213-A, and the patient's risk categories are "No Falls" and "Clear Lungs."

Beneath header area 216 in window 200 is a History table 224. History table 224 has a number of rows in which are shown the date and time that various bed alerts have been detected. In the illustrative example, a Rails alert occurred on Feb. 28, 2009 at 1:54 pm, a Bed Exit alert occurred on Feb. 28, 2009 at 11:34 am, a Brakes alert occurred on Feb. 27, 2009 at 9:56 pm, and another Rails alert occurred on Feb. 26, 2009 at 4:20 pm. Next to table 224 are an up arrow icon 226 and a down arrow icon 228 which are used to scroll up and down the rows of table 224 if there are more rows of information than can fit on table 224 at the same time.

It should be noted that the Alert History for each patient is stored in memory for the duration of their stay at the healthcare facility as determined by information obtained from or sent from the ADT system. During each patient's stay at the healthcare facility, therefore, the alerts information for the patient is stored in computer 10 and/or reporting server 268 but, in some embodiments, is erased as a result of the patient's discharge. Thus, in such embodiments, computer 10 and server 268 do not permanently maintain the alerts information in the way that an EMR system computer may. However, it is within the scope of this disclosure for computer 10 and/or server 268 to communicate the alerts information to the EMR system for longer term storage. Alternatively or additionally, some or all of the data associated with the Alert History for each patient may continue to stored in server 268 and/or computer 10 for a longer period of time after an associated patient's discharge. By continuing to store such historical information, reports can be generated using computer 10 and/or server 268 to determine protocol compliance over time. Healthcare facilities can determine their performance trends, such as with regard to safety protocol compliance, over time by studying such information.

It is contemplated by this disclosure that, in addition to patients being admitted and discharged using the ADT system 264, computer 10 and/or server 264 may be used for one or more of these purposes in some embodiments. For example, manual admit and discharge functions can be performed manually using the keyboard of computer 10. Such admit and/or discharge information entered via computer 10 may be used only locally in connection with the information being gathered and displayed by computer 10, in which case the ADT system 264 still may need to be used for entry of patient admit and discharge information for other purposes. In some embodiments, however, the admit and/or discharge information entered at computer 10 is communicated to other computer devices of facility network 260 including computer devices of the ADT system 264 such that no additional patient admit and/or discharge information needs to be entered by caregivers elsewhere within the network 260.

Window 200 also includes a Bed Alerts Active/Suppress icon 230 that is selected to turn on or turn off whether alerts relating to bed status (e.g., siderail position, caster brake status, bed height) are to be displayed on screen 100 when they occur for the particular patient 218 listed in header area 216. The user simply selects the bed alerts icon 230 to toggle been the active and suppress functions. Window 200 further has a bed icon 232 that provides a graphical image of the current status of the bed associated with the patient 218 listed in header area 216. The graphical appearance of icon 232 mimics the positions of the siderails of the bed and uses color coding such as green and red to indicate the status of bed height and caster brake statuses.

Figure 5:
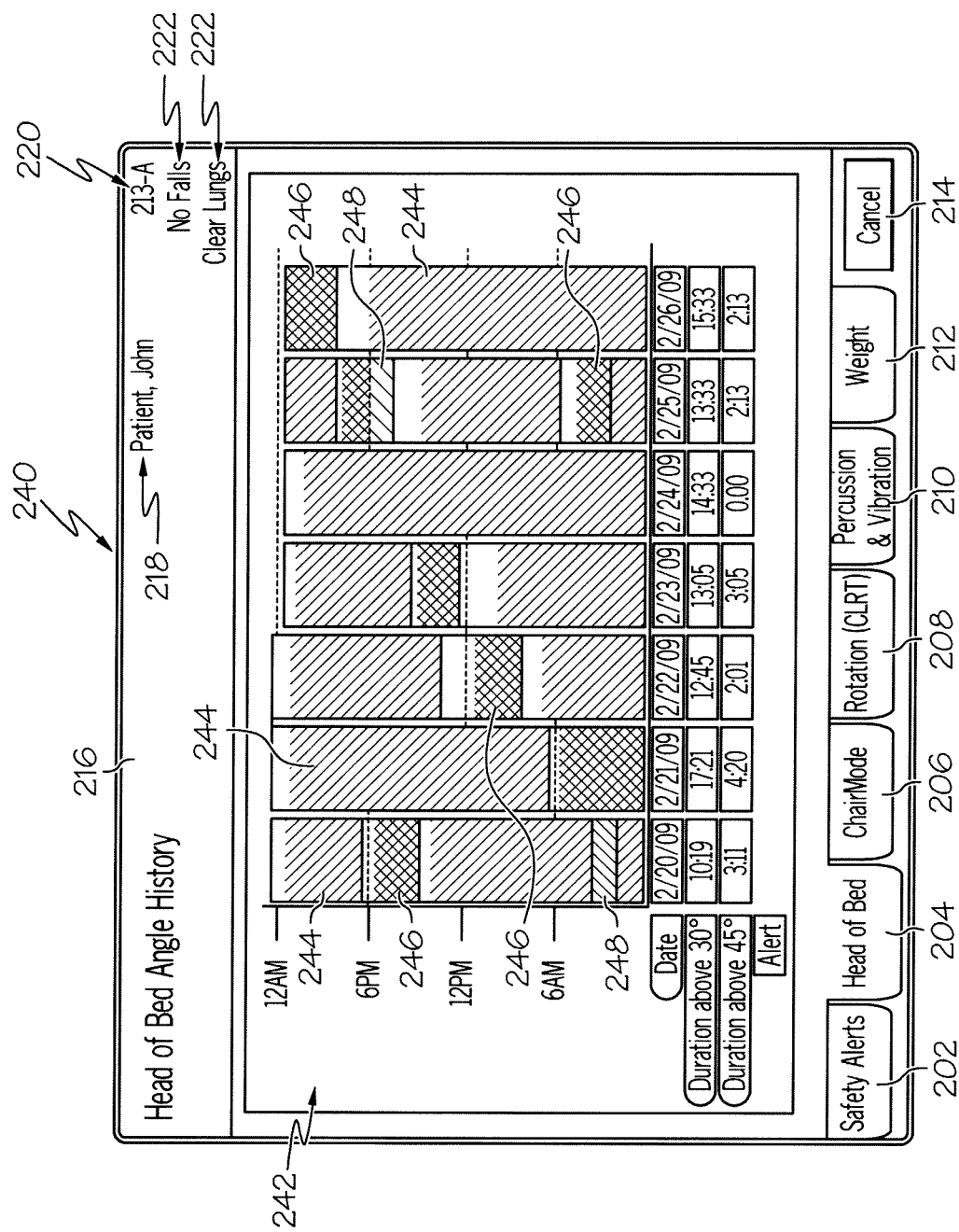
FIG. 5 is a screen shot of an example of a Head of Bed Angle History window.

If a user selects Head of Bed tab 204, computer 10 responds with a Head of Bed Angle History window 240 an example of which is shown in FIG. 5. Window 240 includes the same information in header area 216 as window 200 except that the title on the left hand side of header area 216 is changed to "Head of Bed Angle History." Window 240 has a head of bed angle graph 242 which has columns that correspond to each day of the associated patient's stay at the healthcare facility and that graphically indicates in each column for each day the ranges within which the angle of the head section of the patient's bed 42 was positioned. The ranges are color coded to indicate whether the head section of the bed is above 30 degrees of elevation, above 45 degrees of elevation, or in an alert condition which, in some embodiments, is above 60 degrees of elevation. In one embodiment, the color coding includes green blocks 244 for indicating that the head section was above 30 degrees of elevation, blue blocks 246 for indicating that the head section was above 45 degrees of elevation, and yellow blocks 248 for indicating that the head section was in an alert condition. Other color coding schemes and other graphical representation schemes can be used if desired.

Beneath each column of graph 242 are blocks of information to indicate the date, the duration of time during the 24 hour period of the associated date that the head section of the bed was above 30 degrees, and the duration of time during the 24 hour period that the head section of the bed was above 45 degrees. In some embodiments, an additional block of information is provided to indicate the amount of time during the 24 hour period that the head section of the bed was in an alert condition. It will be appreciated that graph 242 is constructed by computer 10 based on the head of bed angle information that originates at the associated patient bed 42. The historical head of bed information may be stored in memory of computer 10 and/or reporting server 268. The head of bed angle history data used to construct graph 242 begins to be stored in response to receipt of admission data for the patient from the ADT system 264 and ceases to be stored in response to receipt of discharge data for the patient from the ADT system 264.

Figure 6:
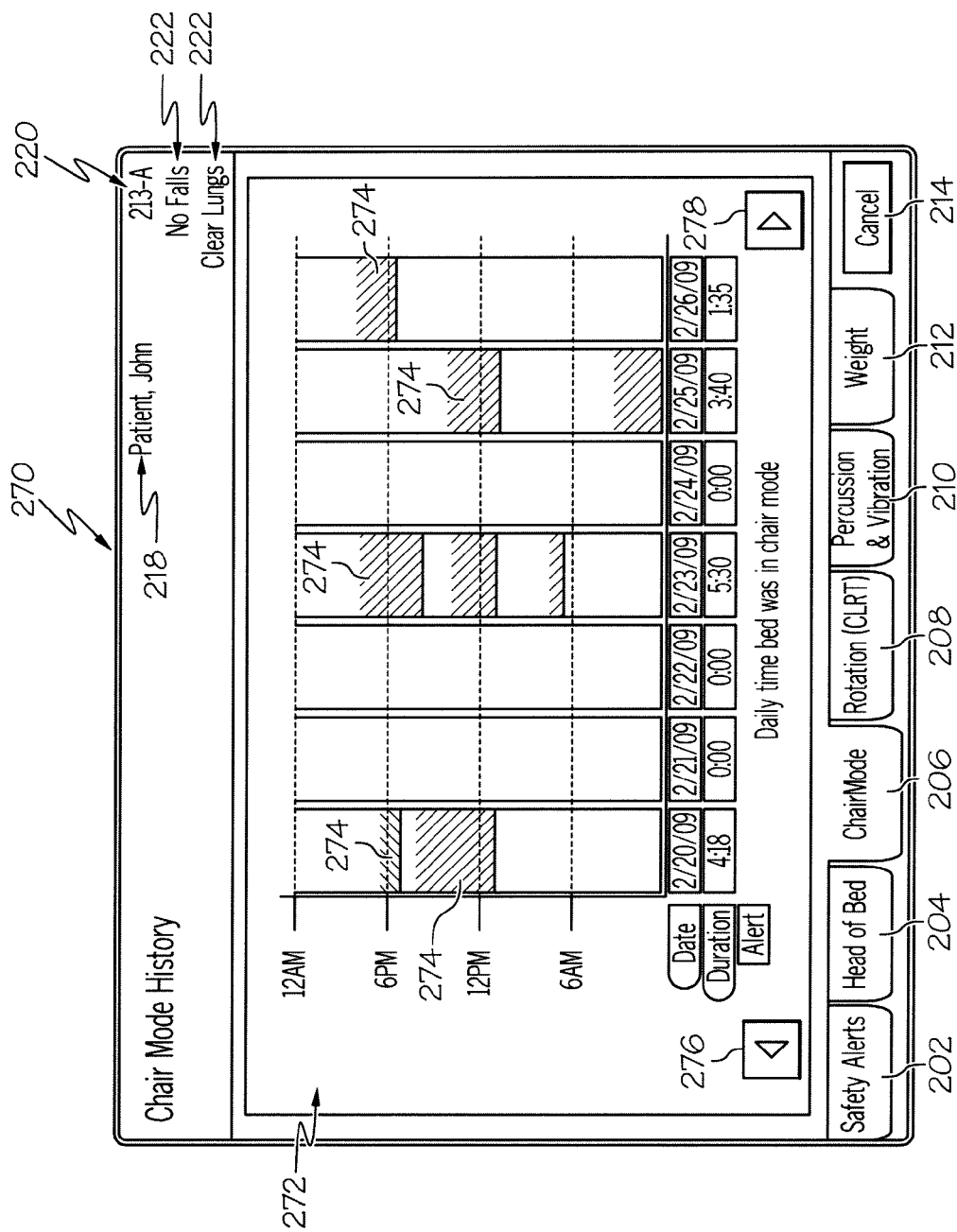
FIG. 6 is a screen shot of an example of a Chair Mode History window.

If a user selects ChairMode tab 206, computer 10 responds with a Chair Mode History window 270 an example of which is shown in FIG. 6. Window 270 includes the same information in header area 216 as windows 200, 240 except that the title on the left hand side of header area 216 is changed to "Chair Mode History." Window 270 has a chair mode graph 272 which has columns that correspond to each day of the associated patient's stay at the healthcare facility and that graphically indicates in each column for each day the times during which the patient's bed 42 was placed in a chair position. The chair position refers to a position in which the head section of bed 42 is raised and the foot section of bed 42 is lowered to place a mattress support deck in a chair like configuration. The times during which the bed 42 is in the chair position are color coded in graph 272. In one embodiment, the color coding includes green blocks 274 for indicating that the bed 42 was in the chair position. Other color coding schemes and other graphical representation schemes can be used if desired.

Beneath each column of graph 272 are blocks of information to indicate the date, the duration of time during the 24 hour period of the associated date that the bed 42 was in the chair position, and whether any alarm associated with the chair position occurred. It will be appreciated that graph 272 is constructed by computer 10 based on information that originates at the associated patient bed 42 to indicate whether the bed is in the chair position. The historical chair position information may be stored in memory of computer 10 and/or reporting server 268. The chair position data used to construct graph 272 begins to be stored in response to receipt of admission data for the patient from the ADT system 264 and ceases to be stored in response to receipt of discharge data for the patient from the ADT system 264. In the illustrative example, a left scroll icon 276 and a right scroll icon 278 are provided near the bottom of window 270 to permit a user to scroll to days that are earlier in time or later in time, respectively, than those currently shown in window 270.

Figure 7:
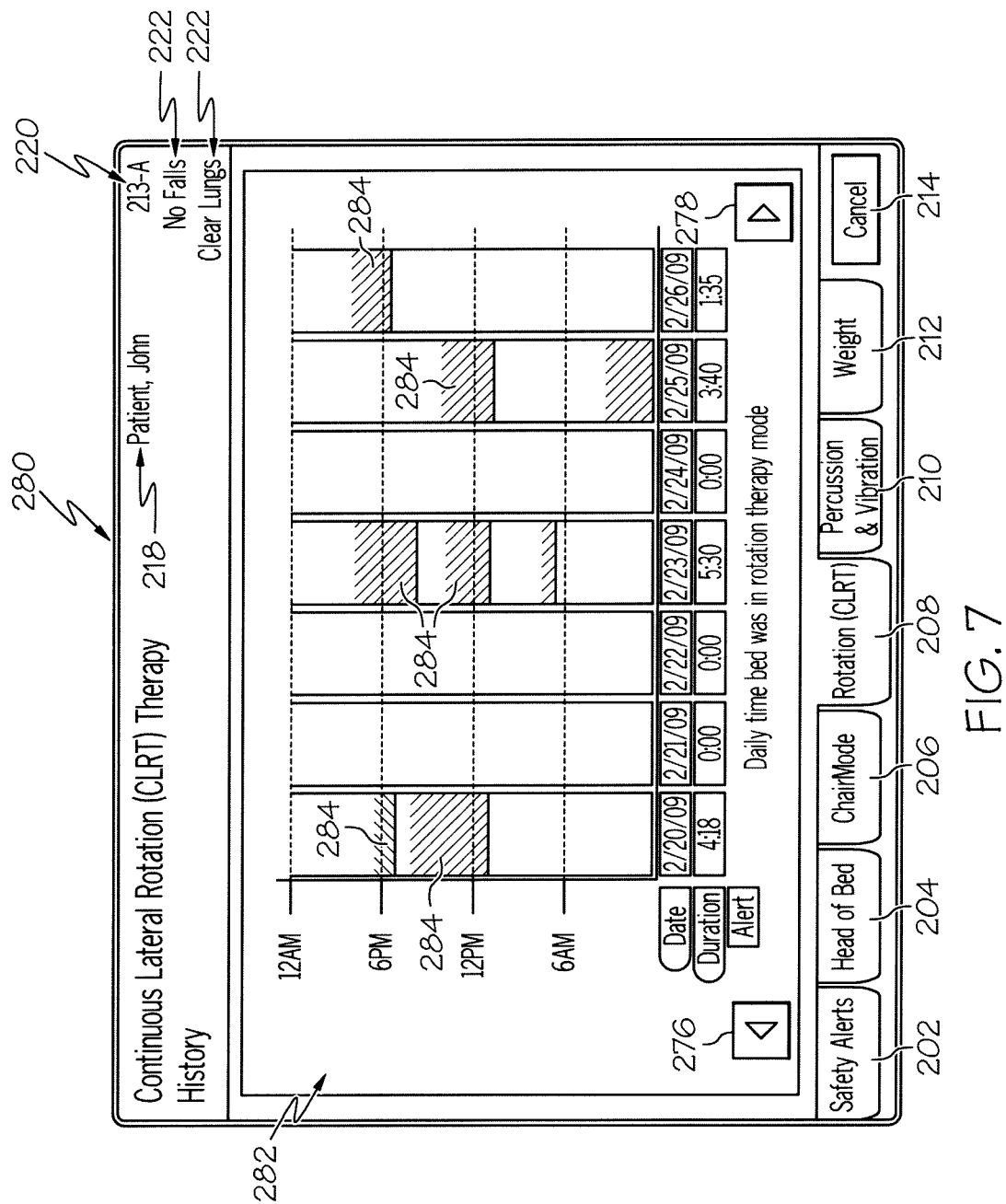
FIG. 7 is a screen shot of an example of a Continuous Lateral Rotation (CLRT) Therapy History window.

If a user selects Rotation (CLRT) tab 208, computer 10 responds with a Continuous Lateral Rotation Therapy (CLRT) History window 280 an example of which is shown in FIG. 7. Window 280 includes the same information in header area 216 as windows 200, 240, 270 except that the title on the left hand side of header area 216 is changed to "Continuous Lateral Rotation (CLRT) Therapy History." Window 280 has a CLRT graph 282 which has columns that correspond to each day of the associated patient's stay at the healthcare facility and that graphically indicates in each column for each day the times during which a mattress on the patient's bed 42 was operating in a CLRT mode. The CLRT mode of a mattress refers to a therapy in which rotation bladders on the left side of the mattress and the right side of the mattress are continuously and alternately inflated and deflated to turn the patient repeatedly to their right and to their left. The times during which the mattress of bed 42 is in operated in the CLRT mode are color coded in graph 282. In one embodiment, the color coding includes green blocks 284 for indicating that the mattress of bed 42 was operating in the chair CLRT mode. Other color coding schemes and other graphical representation schemes can be used if desired.

Beneath each column of graph 282 are blocks of information to indicate the date, the duration of time during the 24 hour period of the associated date that the mattress of bed 42 was operating in the CLRT mode, and whether any alarms associated with the CLRT mode occurred. It will be appreciated that graph 282 is constructed by computer 10 based on information that originates at the associated patient bed 42 to indicate whether the bed is in operating in the CLRT mode. The historical CLRT mode information may be stored in memory of computer 10 and/or reporting server 268. The CLRT mode data used to construct graph 282 begins to be stored in response to receipt of admission data for the patient from the ADT system 264 and ceases to be stored in response to receipt of discharge data for the patient from the ADT system 264. In the illustrative example, window 280 includes left scroll icon 276 and right scroll icon 278 that are used in the same manner as described above to scroll to additional days of information.

Figure 8:
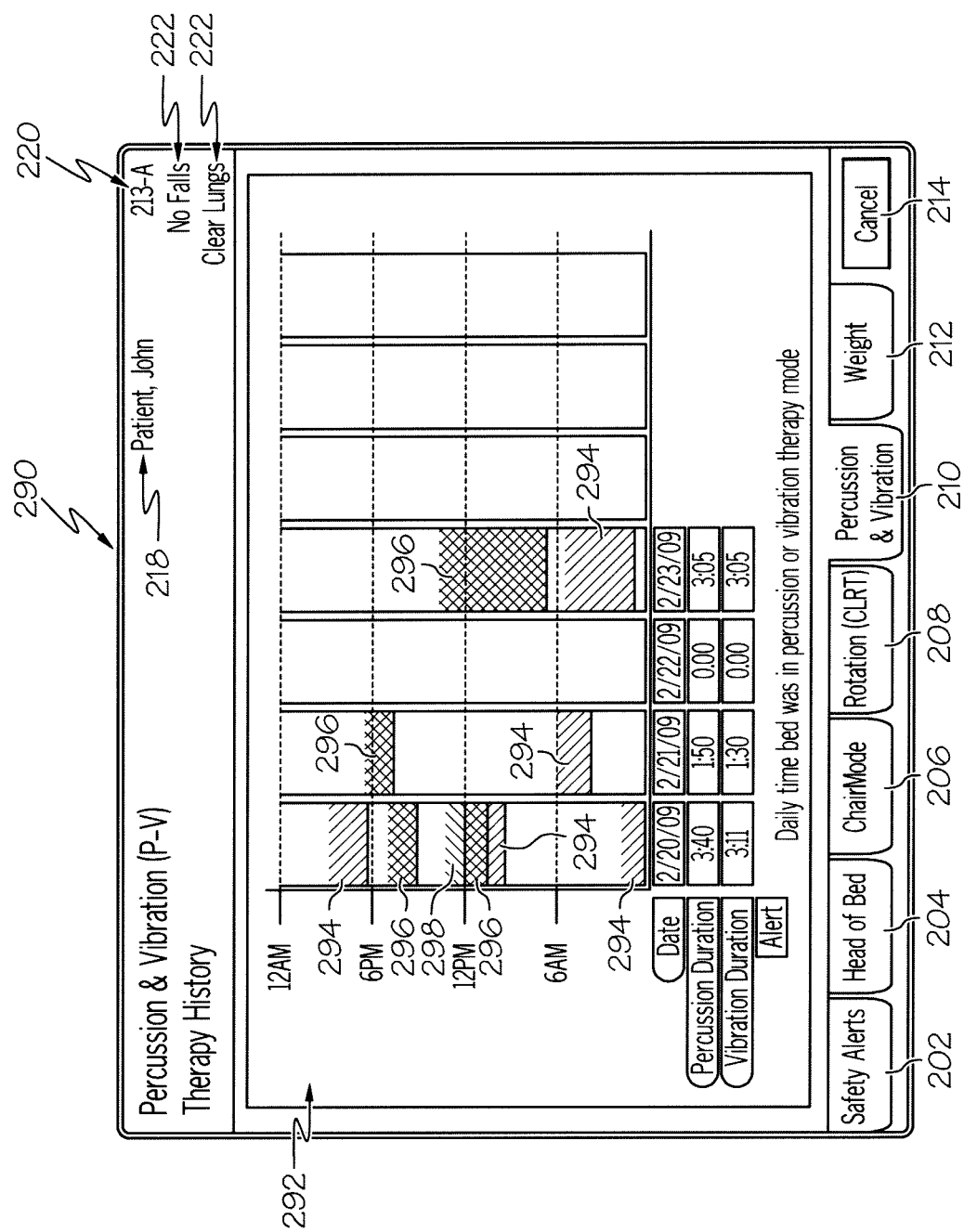
FIG. 8 is screen shot of an example of a Percussion & Vibration (P-V) Therapy History window.

If a user selects Percussion & Vibration tab 210, computer 10 responds with a Percussion & Vibration (P-V) History window 290 an example of which is shown in FIG. 8. Window 290 includes the same information in header area 216 as windows 200, 240, 270, 280 except that the title on the left hand side of header area 216 is changed to "Percussion & Vibration (P-V) Therapy History." Window 290 has a P-V graph 292 which has columns that correspond to each day of the associated patient's stay at the healthcare facility and that graphically indicates in each column for each day the times during which a mattress on the patient's bed 42 was operating in either a percussion mode or a vibration mode. The percussion and vibration modes of a mattress refers to a therapy in which P-V bladders of the mattress are vibrated or percussed. The times during which the mattress of bed 42 is in operated in the P-V modes are color coded in graph 282. In one embodiment, the color coding includes green blocks 294 for indicating that the mattress was operating in the percussion mode, blue blocks 296 for indicating that the mattress was operating in the vibration mode, and yellow blocks 298 for indicating that at least one of the P-V modes was in an alert condition. Other color coding schemes and other graphical representation schemes can be used if desired.

Beneath each column of graph 282 are blocks of information to indicate the date, the duration of time during the 24 hour period of the associated date that the mattress of bed 42 was operating in the percussion mode, the duration of time during the 24 hour period of the associated date that the mattress of bed 42 was operating in the vibration mode, and whether any alarms associated with the P-V modes occurred. It will be appreciated that graph 292 is constructed by computer 10 based on information that originates at the associated patient bed 42 to indicate whether the bed is in operating in one of the P-V modes. The historical P-V mode information may be stored in memory of computer 10 and/or reporting server 268. The P-V mode data used to construct graph 292 begins to be stored in response to receipt of admission data for the patient from the ADT system 264 and ceases to be stored in response to receipt of discharge data for the patient from the ADT system 264. It is contemplated by this disclosure that a similar type of graph can be constructed for other types of therapies associated with beds 42. One example of another time of therapy is alternating pressure (AP) therapy.

Figure 9:
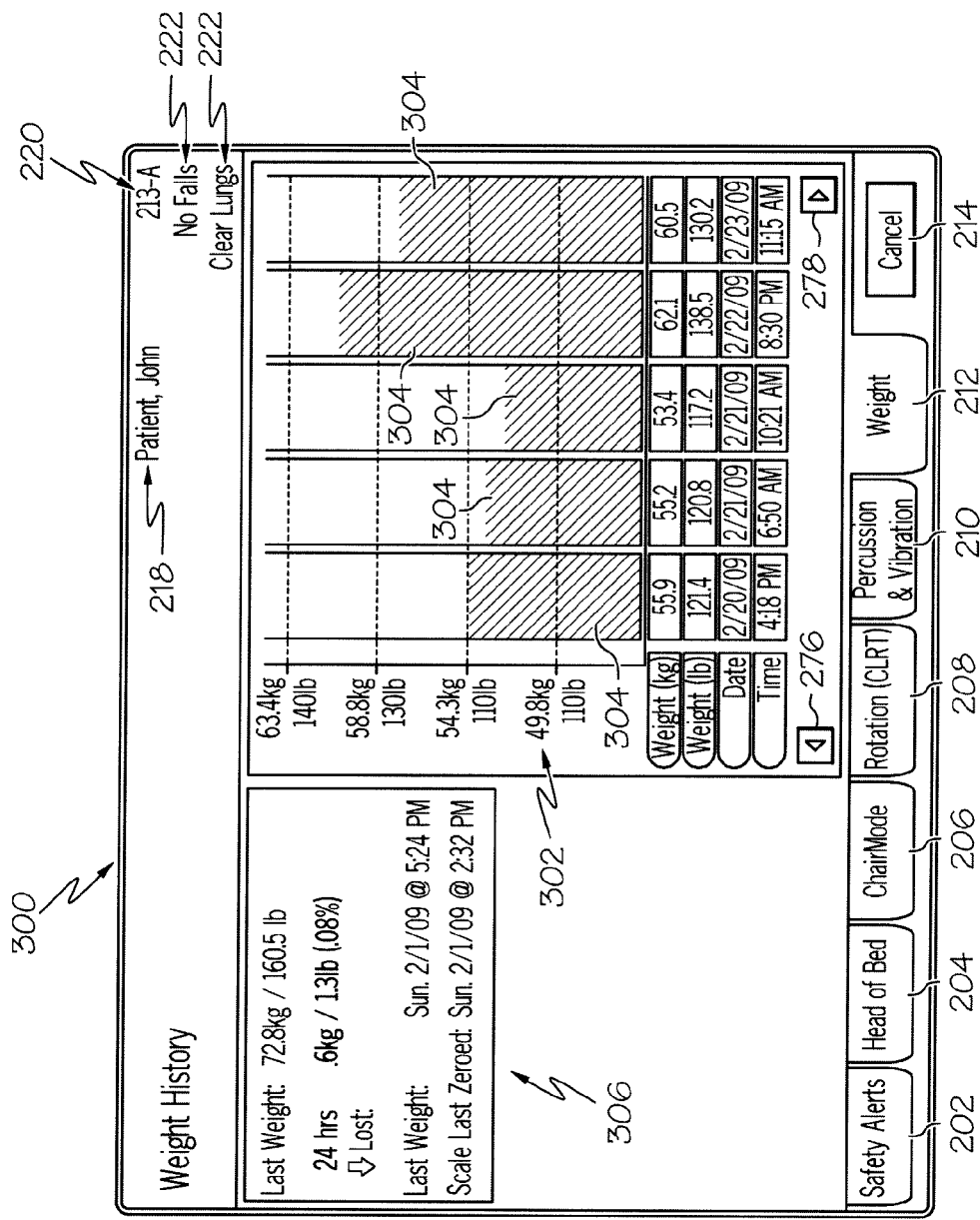
FIG. 9 is a screen shot of an example of a Weight History window.

If a user selects Weight tab 212, computer 10 responds with a Weight History window 300 an example of which is shown in FIG. 9. Window 300 includes the same information in header area 216 as windows 200, 240, 270, 280, 290 except that the title on the left hand side of header area 216 is changed to "Weight History." Window 300 has a weight graph 302 which has columns that correspond to each weight reading taken during the associated patient's stay at the healthcare facility and that graphically indicates in each column the weight measured by the weigh scale system of the patient's bed 42 at the time that the weight was taken. The patient's weight readings are each indicated by a color coded bar 304 in graph 302. In one embodiment, the color coding includes green blocks 304 for indicating the patient's weight reading. Other color coding schemes and other graphical representation schemes can be used if desired.

Beneath each column of graph 302 are blocks of information to indicate the patient's weight reading in kilograms (kg), the patient's weight reading in pounds (lb), the date on which the weight reading was taken, and the time at which the weight reading was taken. It should be noted in the illustrative example of graph 302 that two weight readings were taken on Feb. 21, 2009. Thus, however many weight readings are taken are how many bars are included in graph 304. It is contemplated by this disclosure that, to "take" a weight reading, a caregiver manipulates some sort of user input on bed 42 or the associated patient station 22 or the associated master station 24. In the illustrative example, a left scroll icon 276 and a right scroll icon 278 are provided near the bottom of graph 302 to permit a user to scroll to the weight reading that were taken earlier in time or later in time, respectively, than those currently shown on graph 302.

Each time a weight reading is taken, it is sent to computer 10 and/or reporting server 268 for storage in memory. The weight data used to construct graph 302 is associated with the particular patient when weight readings are taken during the time between which the ADT system 264 indicates that the patient is admitted to and discharged from the healthcare facility. Patient-to-bed association data, which may be entered at master console 24 or computer 10 or some other computer of the facility network 260, including a computer of the ADT system 264, is used to associate the data originating from bed 42, including the weight data, with the proper patient.

Window 300 also includes a table 306 that contains some additional data relating to patient weight. In the illustrative example, table 306 includes the last (aka the most recent) weight reading and includes the weight reading in both kilograms and pounds. Illustrative table 306 further includes the amount of weight change the patient has experienced over the previous 24 hours. In the FIG. 9 example, the patient has lost 0.6 kg or 1.3 lb, which represents a loss of 0.08% of the patient's weight, in the preceding 24 hour period. Illustrative table 306 also includes the date and time which the last weight reading was taken and the date and time at which the scale was last zeroed. Zeroing the scale means that the patient is off of the bed, but all blankets and equipment that will be on the bed with the patient remain on the bed so that a tare weight can be established. The patient's weight is determined relative to the tare weight.

Based on the foregoing, it will be appreciated that computer 10 controls monitor 15 and/or display screen 12 to operate in two primary or main modes of operation. In a first mode of operation, the status board screen 100 is shown on monitor 15 and/or screen 12. In a second mode of operation, one of the history windows 200, 240, 270, 280, 290, 300 is shown on monitor 15 and/or screen 12 and the history windows 200, 240, 270, 280, 290, 300 are accessible via selection of associated tabs 202, 204, 206, 208, 210, 212, 214. When viewing any of windows 200, 240, 270, 280, 290, 300, the user can return to the status board screen 100 by either selecting cancel button 214 in the associated window 200, 240, 270, 280, 290, 300 or by selecting the status board icon 104 which appears in the header bar 102 above whichever is of windows 200, 240, 270, 280, 290, 300 is shown at the time.

Figure 10:
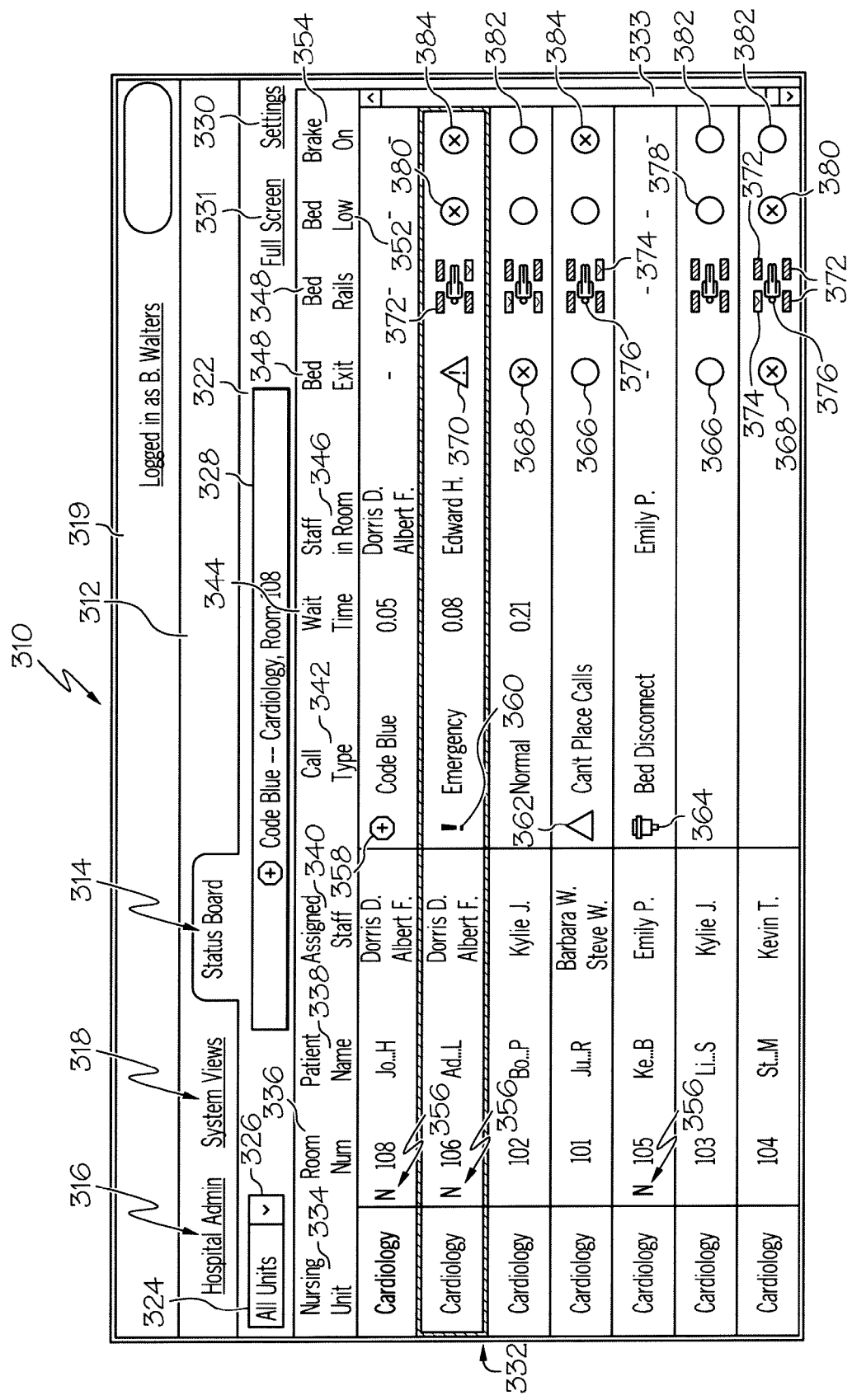
FIG. 10 is screen shot of another example of a status board screen.

Referring now to FIG. 10, an example of an alternative status board screen 310 which is shown on monitor 15 of the status board computer 10 includes a header bar 312 that has a Status Board icon 314, a Hospital Administration icon 316, and a System Views icon 318. A user name bar 319 which is actually above header bar 312 indicates the name of the user that is logged into the bed status system. In the illustrative example of FIG. 10, the text "Logged in as B. Walters"

appears in user name bar 319. Header bar 312 is shown on display 15 at all times that the bed status computer system is operating to permit the user to navigate to the main portion of the system. Thus, when Status Board icon 314 is selected, computer 10 responds with status board screen 310 which is discussed in further detail below.

When Hospital Administration icon 316 is selected, computer 10 responds with an administration screen (not shown) that permits a hospital administrator to enter a user name and password to gain access to various other screens to set up new users of the system, for example. In some embodiments, such other screens also permit the administrator to add caregivers to the list of assignable caregivers and to assign particular caregivers to patients and/or to rooms in the nursing unit. In other embodiments, the caregiver assignments to patients and/or rooms are made using the associated master console 24 and then that data is communicated to bed status computer 10 so that the assignment information can be properly shown on screen 310. When System Views icon 318 is selected, computer 10 responds with the types of screens which are shown, for example, in FIGS. 4-9 and which were discussed above.

In the illustrative status board screen 310, a display control area bar 322 appears beneath header bar 312 but above a main table 332. Illustrative display control area bar 322 includes an Unit identifier block 324, a Unit Selector icon 326, a Dynamic Message Area box 328, and a Settings icon 330 and a Full Screen icon 331. The Unit identifier block 324 in the illustrative example indicates the user has selected to view the data associated with All Units. If the user selects the Unit Selector icon 326, then computer 10 responds with a drop down menu in the vicinity of block 324 that has a list of the nursing units that may be view on status board screen 310. For example, such a drop down menu may include a list such as Cardiology, Unit 1, Unit 2, All Units. The user then selects in the drop down menu the unit or units for which the user desired the data to be displayed on screen 310.

The Dynamic Message Area box 328 shows any calls that have been received from any of the rooms in the nursing unit or units listed in block 324. If there are multiple calls and multiple call types, then the calls are prioritized and appear in Dynamic Message Area box 328 in the same manner as described above in connection with Dynamic Message Area box 118 of screen 100 shown in FIG. 3. In the example of FIG. 10, box 118 contains the text "Code Blue—Cardiology, Room 108" and there is an octagon with a plus sign icon in front of the text to indicate a code blue situation. It is contemplated by this disclosure that the amount of time that has elapsed since a particular call has been placed can be included in box 328 during the time that the associated call or alert is displayed in box 328, although in the illustrative example, the elapsed time does not appear in box 328. As was the case with box 118 described above, it should be understood that the particular text used for a particular type of call shown in box 328 is at the discretion of the system programmer and may even be configurable by a hospital administrator such that the examples given herein are intended to be illustrative of the basic idea.

In some embodiments, the amount of time that has elapsed is referred to as a Call Threshold Indicator and may be a number that is preprogrammed or that is preselected by a hospital administrator. For example, a Call Threshold Indicator may be set at 15 minutes. Thus, after a call occurs, the elapsed time since the call is not displayed in box 328 until after the threshold amount of time has elapsed. After the threshold amount of time has elapsed, which in the given example is 15 minutes, then the time since the call was placed is indicated in box 328.

Figure 11:
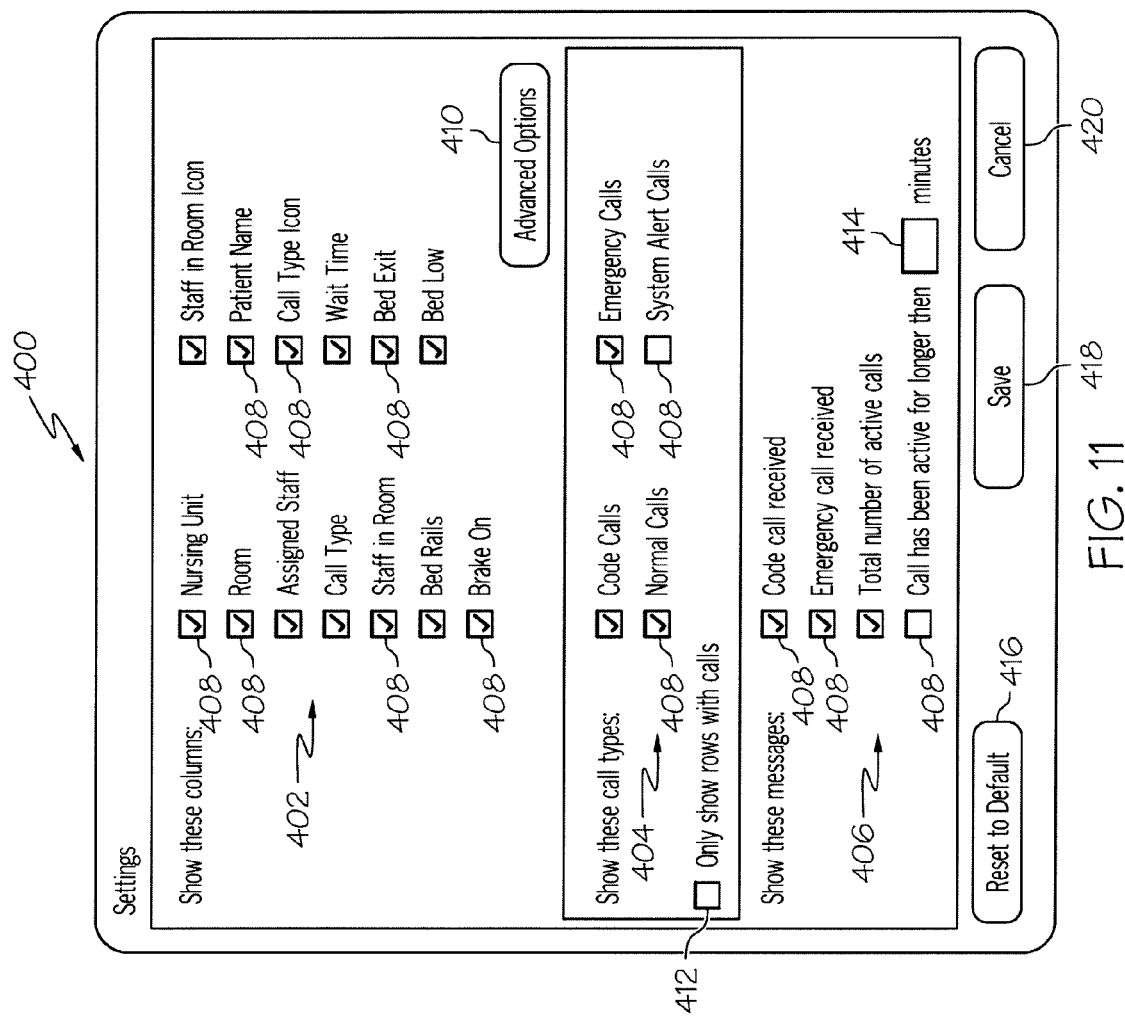
FIG. 11 is a screen shot of an example of a Settings window which is used to select the type of information to be shown on the status board screen.

If a user selects Settings icon 330 on screen 310, computer 10 responds with a Settings window 400 an example of which is shown in FIG. 11. Window 400 includes a set of columns choices 402 that are generally grouped together, a set of call type choices 404 that are generally grouped together, and a set of message choices 406 that are generally grouped together. Each of the various choices 402, 404, 406 is selectable and deselectable by the user of computer 10 by checking or unchecking, as the case may be an associated check box 408 that is adjacent to each of the choices 402, 404, 406. If a user selects Full Screen icon 331, screen 310 occupies the full amount of the area of monitor 15 and display screen 12.

In the illustrative example of FIG. 11, columns choices 402 include the following choices: Nursing Unit Room, Assigned Staff, Call Type, Staff in Room, Bed Rails, Brake On, Staff in Room Icon, Patient Name, Call Type Icon, Wait Time, Bed Exit, and Bed Low. An Advanced Options button or icon 410 appears on screen 400 near the columns choices 402. If a user selects the Advanced Options button then additional user choices can be made such as, for example, changing the order in which the columns appear on screen 310, changing the font type or size of the text that appears in the columns, and so on. In the illustrative example, call types choices 404 include the following choices: Code Calls, Normal Calls, Emergency Calls, and System Alert Calls. An additional check box 412 appears in the vicinity of choices 404 in window 400 and can be selected by a user to only show rows with calls. In the illustrative example, box 412 is deselected as indicated by the absence of a check mark in box 412. Also in the illustrative example of FIG. 11, the messages choices include the following choices: Code call received, Emergency call received, Total number of active calls, and Call has been active for longer than _____ minutes. The blank in the last message choice corresponds to a text box 414 in which a user may enter a number of minutes at which the particular message is to be triggered if a call has remained active.

Widow 400 also includes a Reset to Default button or icon 416, a Save button or icon 418, and a Cancel button or icon 420. If a user selects the Reset to Default icon 146, then certain ones of the choices 402, 404, 406 are selected as the default and the associated check boxes 408 are populated with check marks. The check boxes appearing in FIG. 11 correspond to the default setting. One of the options associated with the Advanced Options icon 410 is the ability of the user to change the default choices. If a user selects the Save icon 418, then the user's various selections and deselections made while window 400 was opened are saved and implemented and then, window 400 automatically closes to return the user back to screen 310. If the user selects the Cancel icon 420, then the user's various selections and deselections made while window 400 was opened are undone and ignored, the settings that existed prior to the user opening window 400 are restored, and then, window 400 automatically closes to return the user back to screen 310.

Main table 332 occupies the majority of screen 310 and includes rows that correspond to each room in the nursing unit or units that have been selected via icon 326 for display. In the illustrative example in which All Units have been chosen for display, there is only room on table 332 for seven rows of information. In the example of FIG. 10, rooms 101-106 and room 108 of the Cardiology unit can be seen on table 332. Thus, because there are more rooms in the selected nursing units than are able to fit onto the viewing area of main table 332, a scroll bar 333 appears at the left side of table 332 to permit the user to scroll up and down to see the additional rooms. Main table 332 includes the following columns of information: a Nursing Unit column 334, a Room Number column 336, a Patient Name column 338, an Assigned Staff column 340, a Call Type column 342, a Wait Time column 344, a Staff in Room column 346, a Bed Exit column 348, a Bed Rails column 350, a Bed Low column 352, and a Brake On column 354.

The Nursing Unit column 334 simply lists the name of the nursing unit in which the room and other information of the associated row correspond. In the illustrative example of FIG. 10, Cardiology is the unit for all of the rows shown in table 332.

The Room Number column 336 shows the number of the room associated with each row of information. Table 332 has the rows sorted based on the type of call that is received. In particular, rooms having code blue calls are listed first, then rooms having emergency calls, then rooms having normal calls, then rooms having equipment status alerts, and finally, rooms having not alerts. Thus, in the illustrative example, the order of the rooms appears to be somewhat jumbled and is as follows: 108, 106, 102, 101, 105, 103, 104. However, that is simply a consequence of sorting the table based on call type. Also of note with regard to the example of FIG. 10 are the Staff in Room icons 356 which appear just to the left of the room number in three of the rows, namely, the rows of rooms 108, 106 and 105. The Staff in Room icon 356 of the illustrative example is the letter "N."

The Patient Name column 338 shows, for each of the rooms that contain a patient, a patient identifier in a HIPAA compliant format. In the illustrative example, a partial patient name is shown by indicating the first two letters of the patient's last name followed by a set of ellipses and the first letter of the patient's first name. While each room in table 332 of FIG. 10 has a patient in the room, the Room Ready and Not Ready messages discussed above in connection with table 122 are also used under similar circumstances in table 332.

The Assigned Staff column 340 lists the names of the caregivers who are assigned to patients in each of the rooms. As can be seen in FIG. 10, some patients have two assigned caregivers and others only have one assigned caregiver. In the illustrative example, the caregiver names are listed in last name, first initial format.

Call Type column 342 shows the type of call, if any, that has been placed or that has otherwise been detected for each room in the unit or units being viewed in table 332. Next to Call Type column 342 is the Wait Time column 344 which indicates the amount of time that elapsed after the call in column 342 was placed until a caregiver entered the associated room to attend to the call. Column 344 is only populated with wait times for code blue calls, emergency calls, and normal calls.

In the illustrative example, a Code Blue call was placed from room 108 and it took 5 seconds for a caregiver to respond, an Emergency call was placed from room 106 and it took 8 seconds for a caregiver to respond, and a Normal call was placed from room 102 and 21 second have elapsed since the call. A code blue icon 358 appears to the right of the "Code Blue" text in column 342 and an emergency icon 360, illustratively an exclamation point, appears to the right of the "Emergency" text in column 342. With regard to Normal calls, a suitable caregiver response sometimes involves nothing more than speaking with the patient using the communications capability of the nurse call system. Thus, the wait time for normal calls in some embodiments is the amount of time it takes for a caregiver to open up a communication channel to the room from which the Normal call originated.

In the FIG. 10 example, there are two equipment status alerts that appear in table 332. Specifically, there is a "Can't Place Calls" alert occurring in room 101 and a "Bed Disconnect" alert occurring in room 105. The "Can't Place Calls" alert may be occurring, for example, due to a malfunction associated with a nurse call button on a bed siderail or on a pillow speaker unit. A can't place calls icon 362, illustratively a triangle, appears to the right of the "Can't Place Calls" text in column 342. The "Bed Disconnect" alert means that the associated bed 42 has been disconnected from the respective connector unit 40. A bed disconnect icon 364 appears to the right of the "Bed Disconnect" text in column 342.

The Staff in Room column 346 lists the names of the caregivers or other staff members who are physically present in the associated patient rooms. In the illustrative example, Dorris D. and Albert F. are present in room 108, Edward H. is present in room 106, and Emily P. is present in room 105. For each of the rooms in which a staff member is present, the staff in room icon 356 appears in column 336 as mentioned previously. It should be noted that, with regard to room 106, the staff member that is present in room 106 is not one of the staff members that is assigned to that particular room. However, the likely reason for that in the given example is that the two staff members assigned to room 106 are also assigned to room 108 where the code blue is occurring. Thus, both caregivers assigned to room 108 are present in that room to attend to the code blue situation.

It will be appreciated that computer 10 receives information from a locating and tracking system of the healthcare facility in order to determine the identities of the staff members that are present in each of the rooms. Based on that information, the information in row 346 is populated accordingly and the appropriate staff in room icons are added to column 336. As mentioned previously, the locating and tracking system includes, for example, badges 58 and room locating receivers 56 which are described above. The locating and tracking information is stored in reporting server 268 in some embodiments.

The Bed Exit column 348 indicates whether or not a bed exit system of the hospital bed 42 associated with the patient of each row of table 332 is armed, at what level it is armed, and whether a bed exit alarm is occurring. In the illustrative example, there are three levels of bed exit sensitivity that can be chosen when the bed exit system of a particular bed 42 is armed. Those levels are patient position mode, bed exiting mode, and out-of-bed mode. When the bed exit system of an associated patient bed 42 is armed, then a bed exit armed icon 366 appears in column 348 as shown in table 332 with regard to rooms 101 and 103. In the illustrative example, the bed exit armed icon 366 is a circle. Icon 366 is color coded to indicate which of the levels of bed exit sensitivity is chosen. For example, patient position mode may be color coded green, bed exiting mode may be color coded yellow, and out of bed mode may be color coded red. When the bed exit system of an associated bed is not armed, then a bed exit unarmed icon 368 appears in column 348 as sown in table 332 with regard to rooms 102 and 104. In the illustrative example, the bed exit unarmed icon 368 is a circle with an "x" inside of it.

Column 348 also includes an alarm indicator 370, illustratively a triangle with an exclamation point inside of it, to indicate that a bed exit alarm is occurring. Icon 370 is color coded in some embodiments to indicate whether the alarm that is occurring but has been silenced. For example, icon 370 may be color coded red if the alarm is occurring and has not been silenced and may be color coded yellow if the alarm is occurring and has been silenced. The data shown in column 348 is based on information transmitted from the beds 42 located in the patient rooms of the nursing unit for which the information viewed on monitor 15 and/or display screen 12 is associated. As mentioned previously, the bed exit systems are typically armed by caregivers at the bedside by manipulating the appropriate bed exit user interface devices, such as buttons or touch screen, found on the individual beds 42. However, as also mentioned previously, it is within the scope of this disclosure for the bed exit systems of beds 42 to be armed via some other user input device or computer device such as stations 22, 24.

The Bed Rails column 350 indicates for each of the hospital beds 42 in each of the patient rooms, whether the siderails of the bed 42 are in a raised position or in a lowered position. In the illustrative example of FIG. 10, there are four rectangular indicators provided in each row with each individual rectangle corresponding to one of the four siderails of the associated hospital bed 42. There are two different types of rectangular indicators, however. Namely, an up indicator 372 to indicate that the corresponding siderail of the bed 42 is in a raised position and a down indicator 374 to indicate that the corresponding siderail of the bed 42 is in a lowered position.

A patient icon 376 is also provided in column 350 to indicate the relative locations of the siderails relative to the patient and associated bed 42. In those instances when a particular bed 42 has a different number of siderails, such as having only two siderails for example, then a corresponding number of rectangular indicators are provided in column 140. The data shown in column 350 is based on information transmitted from the beds 42 located in the patient rooms of the nursing unit for which the information viewed on monitor 15 and/or display screen 12 is associated. It is contemplated by this disclosure that, in some embodiments, patient icon 376 is color coded to indicate the patient's presence in the associated bed 42. For example, when the bed exit system of bed 42 detects that the patient is in the bed, icon 376 is color coded green in some embodiments. When the patient is not in bed, icon 376 is color coded in some other manner such as red or white.

The Bed Low column 352 includes a Low indicator or icon 378 to indicate that an upper frame of the bed 42 is in its lowest position relative to a base frame of the bed 42 and a Not Low indicator or icon 380 to indicate that the upper frame of the bed 42 is not in its lowest position relative to the base frame. In the illustrative example, Low icon 378 can be seen with regard to rooms 101, 102, 103 in table 332 and Not Low icon 380 can be seen with regard to rooms 104, 106 in table 332. Also illustratively, the Low icon 378 is a circle and the Not Low icon 380 is a circle with an "x" in it. The data shown in column 352 is based on information transmitted from the beds 42 located in the patient rooms of the nursing unit for which the information viewed on monitor 15 and/or display screen 12 is associated.

The Brake On column 354 includes a Brake On indicator or icon 382 to indicate that the casters of the associated bed 42 are braked and a Brake Off indicator 384 to indicate that the casters of the associated bed 42 are not braked. In the illustrative example, Brake On icon 382 can be seen with regard to rooms 102, 103, 104 in table 332 and Brake Off icon 384 can be seen with regard to rooms 101, 106 in table 332. Also illustratively, the Brake On icon 382 is a circle and the Brake Off icon 384 is a circle with an "x" in it. The data shown in column 354 is based on information transmitted from the beds 42 located in the patient rooms of the nursing unit for which the information viewed on monitor 15 and/or display screen 12 is associated.

With regard to columns 348, 350, 352, 354, if a dash appears in those columns, it means that the associated bed 42 does not have the capability to provide the associated type of data or that the bed 42 is disconnected in that particular room. In the illustrative example, the bed 42 in room 108 is not a capable of providing any of the types of data that would otherwise be populated in columns 348, 350, 352, 354 and the bed 42 in room 105 has been disconnected.

When it is stated herein that a user or caregiver "selects" an icon or button on a particular screen or display, or similar such words are used such as "selected" and "selecting" in a similar context, all methods of selecting a button or icon on a screen or display are intended to be covered. For example, selections can be made by moving a computer mouse to place a cursor over a button or icon and then a button on the mouse can be clicked or pressed or double-clicked, for example. Other methods of selecting buttons or icons within the scope of this disclosure include using the tab or arrow keys on a computer keyboard to highlight the desired icon or button and then pressing the enter key of the keyboard or by touching the screen, such as with a finger, stylus, or light pen, on the area of the screen on which the desired button or icon is displayed.

According to this disclosure, certain pop-up windows with information appear when a user hovers over a particular button or icon. In this regard, to "hover" or "hovering" means to use a computer mouse to place a cursor over an icon or button for a short threshold period of time (e.g., on the order of one or two seconds) without clicking any buttons of the mouse. With regard to table 332 of screen 310, when a user hovers over the Assigned Staff icon 340 or above the Staff in Room icon 346, a pop-up window appears listing the assigned or located staff, as the case may be, along with their titles, which are abbreviated in some embodiments, and their extension. The staff extension means a phone number or other numeric code that is dialed or entered on a phone keypad to reach a wireless communication device, such as a wireless handset or Vocera™ badge, which is carried by the particular staff member. Also with regard to table 332 of screen 310, when user hovers over the Call Type icon 342, a pop-up window appears listing all of the active calls and the duration of the calls.

Although certain illustrative embodiments have been described in detail above, variations and modifications exist within the scope and spirit of this disclosure as described and as defined in the following claims.

The invention claimed is:

1. A healthcare information system for use in a healthcare facility having patient beds in a plurality of patient rooms, the healthcare information system comprising
 a nurse call computer located at a nurse's station, the nurse call computer including a first display screen, the nurse call computer being configured to receive nurse calls originating from the patient rooms and to display information about the nurse calls on the first display screen,
 a plurality of interface units, each interface unit being located in an associated patient room, each interface unit being configured to receive bed data that pertains to an associated patient bed, each interface unit communicatively coupled to the nurse call computer and configured to send bed data to the nurse call computer automatically without any user input at the associated interface unit, and
 a status board computer also located at the nurse's station, the status board computer being communicatively coupled to the plurality of interface units, the status board computer comprising a second display screen that is operable in a first mode to display simultaneously, for more than one patient, in a single row format for each of the more than one patient, information regarding the patient, name of any located staff in the patient's room, bed data, and room status, wherein the status board computer is configured to permit a user to select and deselect which information from among all available information is to be shown on the second display screen when it is later operating in the first mode and to omit from being shown that information which is deselected, wherein for each patient for whom an alert or nurse call has been generated, the second display screen shows in each respective row an alert/call type and an elapsed time, in seconds, since each individual alert or nurse call was generated.

2. The healthcare information system of claim 1, wherein the second display screen, when being operated in the first mode, displays for more than one patient graphical indicia indicating the position of multiple bed siderails.

3. The healthcare information system of claim 1, wherein the second display screen, when being operated in the first mode, displays for more than one patient graphical indicia indicating whether a bed exit alarm is activated.

4. The healthcare information system of claim 1, wherein the second display screen, when being operated in the first mode, displays for more than one patient a timer indicating the amount of time that has elapsed since a caregiver has last entered each of the rooms of the more than one patient.

5. The healthcare information system of claim 1, wherein the second display screen, when being operated in the first mode, displays for more than one patient head of bed angle data.

6. The healthcare information system of claim 1, wherein the status board computer is communicatively coupled to the plurality of interface units via a network switch.

7. The healthcare information system of claim 6, wherein the status board computer is communicatively coupled to the plurality of interface units via a Power over Ethernet (PoE) switch.

8. The healthcare information system of claim 1, wherein the status computer and the nurse call computer are communicatively coupled to the plurality of interface units via a Power over Ethernet (PoE) switch.

9. The healthcare information system of claim 1, wherein the second display screen is operable in a second mode to display a safety alert history for a selected one of the patients.

10. The healthcare information system of claim 9, wherein the safety alert history includes a date and a time at which any siderails of the patient bed associated with the selected one of the patients has been lowered.

11. The healthcare information system of claim 9, wherein the safety alert history includes a date and a time at which any bed exit alerts from the patient bed associated with the selected one of the patients has been generated.

12. The healthcare information system of claim 9, wherein the safety alert history includes a date and a time at which a caster brake of the patient bed associated with the selected one of the patients has been released.

13. The healthcare information system of claim 1, wherein the second display screen is operable in a second mode to display a chair mode history for a selected one of the patients to show a date and a time during which the patient bed associated with the selected one of the patients has been in a chair position.

14. The healthcare information system of claim 1, wherein the second display screen is operable in a second mode to display a continuous lateral rotation therapy (CLRT) history for a selected one of the patients to show a date and a time during which the patient bed associated with the selected one of the patients was operated in a CLRT mode.

15. The healthcare information system of claim 1, wherein the second display screen is operable in a second mode to display a percussion and vibration therapy (P-V) history for a selected one of the patients to show a date and a time during which the patient bed associated with the selected one of the patients was operated in one or more of a percussion mode and a vibration mode.

16. The healthcare information system of claim 1, wherein the second display screen is operable in a second mode to display a weight history for a selected one of the patients to show a date, a time, and a weight reading made by a scale system of the patient bed associated with the selected one of the patients.

17. The healthcare information system of claim 1, wherein the second display screen when operating in the first mode shows information regarding those patients only for whom an associated one of the alert or nurse calls has been generated.

18. The healthcare information system of claim 1, wherein the alert/call type comprises one of a safety alert call type, a normal call type, and a code blue call type.

19. The healthcare information system of claim 1, wherein the second display screen is operable in a second mode to display history information including at least one of a safety alert history, a chair mode history, a continuous lateral rotation therapy (CLRT) history, a percussion and vibration therapy (P-V) history, and a weight history; the bed status computer begins gathering the history information for each patient in response to the bed status computer receiving admission information from an Admission Discharge and Transfer (ADT) system; and the bed status computer terminates gathering the history information for each patient in response to the bed status computer receiving discharge information from the ADT system.

* * * * *